US010487085B2

(12) United States Patent
Yamamoto et al.

(10) Patent No.: US 10,487,085 B2
(45) Date of Patent: *Nov. 26, 2019

(54) PURINONE DERIVATIVE

(71) Applicant: ONO PHARMACEUTICAL CO., LTD., Osaka (JP)

(72) Inventors: Shingo Yamamoto, Osaka (JP); Toshio Yoshizawa, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/269,744

(22) Filed: Feb. 7, 2019

(65) Prior Publication Data
US 2019/0169192 A1 Jun. 6, 2019

Related U.S. Application Data

(60) Continuation of application No. 15/895,036, filed on Feb. 13, 2018, now Pat. No. 10,233,185, which is a division of application No. 15/648,941, filed on Jul. 13, 2017, now Pat. No. 9,926,322, which is a continuation of application No. 14/564,568, filed on Dec. 9, 2014, now Pat. No. 9,879,013, which is a continuation of application No. 13/700,774, filed as application No. PCT/JP2011/062377 on May 30, 2011, now Pat. No. 8,940,725.

(30) Foreign Application Priority Data

May 31, 2010 (JP) ................ 2010-123727

(51) Int. Cl.
A01N 43/00 (2006.01)
A61K 31/00 (2006.01)
C07D 473/34 (2006.01)
A61K 31/522 (2006.01)

(52) U.S. Cl.
CPC .......... C07D 473/34 (2013.01); A61K 31/522 (2013.01)

(58) Field of Classification Search
None
See application file for complete search history.

(56) References Cited

U.S. PATENT DOCUMENTS

| | | | |
|---|---|---|---|
| 7,071,199 B1 | 7/2006 | Hirst et al. | |
| 8,557,803 B2 | 10/2013 | Yamamoto et al. | |
| 8,940,725 B2 | 1/2015 | Yamamoto et al. | |
| 2003/0171360 A1 | 9/2003 | Gross et al. | |
| 2008/0076921 A1 | 3/2008 | Honigberg et al. | |
| 2013/0079327 A1 | 3/2013 | Yamamoto et al. | |
| 2013/0217880 A1 | 8/2013 | Yamamoto et al. | |
| 2014/0303191 A1 | 10/2014 | Buggy et al. | |
| 2014/0330015 A1 | 11/2014 | Yamamoto et al. | |
| 2015/0125446 A1 | 5/2015 | Klein et al. | |

FOREIGN PATENT DOCUMENTS

| | | |
|---|---|---|
| CA | 2 800 523 | 12/2011 |
| CA | 2 857 150 | 6/2013 |
| JP | 2003-509427 | 3/2003 |
| JP | 2010-504324 | 2/2010 |
| WO | 2001/019828 | 3/2001 |
| WO | 2003/037890 | 5/2003 |
| WO | 2005/011597 | 2/2005 |
| WO | 2007/142755 | 12/2007 |
| WO | 2008/060301 | 5/2008 |
| WO | 2008/121742 | 10/2008 |
| WO | 2010/009342 | 1/2010 |
| WO | 2011/018224 | 2/2011 |
| WO | 2011/152351 | 12/2011 |
| WO | 2013/081016 | 6/2013 |
| WO | 2014/081712 | 5/2014 |
| WO | 2014/194254 | 12/2014 |
| WO | 2016/024230 | 2/2016 |

OTHER PUBLICATIONS

International Search Report dated Aug. 16, 2011 in International (PCT) Application No. PCT/ JP2011/062377.
Vetrie, David, et al., "The gene involved in X-linked agammaglobulinaemia is a member of the src family of protein-tyrosine kinases", Nature, vol. 361, Jan. 21, 1993, pp. 226-233.
Uckun, Fatih M., et al., "Bruton's Tyrosine Kinase as a New Therapeutic Target", Anti-Cancer Agents in Medicinal Chemistry, vol. 7, 2007, pp. 624-632.
Supplementary European Search Report dated Sep. 19, 2013 in European Application No. 11 78 9754.
Anderson, Chem. and Biol., vol. 10, 2003, pp. 787-797.
CAS RN 1222785810, entered STN May 13, 2010.
Yasuhiro et at, "ONO-4059, a novel oral Bruton's tyrosine kinase (Btk) inhibitor that demonstrates potent pharmacodynamic activity through Phosphorylated Btk (P-Btk) inhibition, in addition to effective anti-tumour activity in a TMD-8 (DLBCL) xenograft model", American Association for Cancer Research Annual Meeting 2013, Abstract No. 2452.
Rule et al., "A Phase I Study of the Oral Btk Inhibitor ONO-4059 in Patients With Relapsed/Refractory B-Cell Lymphoma", 55th American Society of Hematology, session: 624, program No. 4397, 2013.
Dyer et al., "The Bruton's tyrosine kinase (BTK) inhibitor ONO-4059: Single-agent activity in patients with relapsed and refractory non-GCB-DLBCL", 2014 ASCO Annual Meeting, Abstract No. 8553.

(Continued)

Primary Examiner — Jared Barsky
(74) Attorney, Agent, or Firm — Wenderoth, Lind & Ponack, L.L.P.

(57) ABSTRACT

Compounds represented by general formula (I) (all of the symbols in the formula conform to the definitions in the Description) are compounds that, in addition to having a Btk-selective inhibitory activity, exhibit an excellent metabolic stability and can avoid hepatotoxicity or the like, and as a consequence can provide safe therapeutic agents for diseases in which B cells or mast cells participate.

2 Claims, No Drawings

(56) References Cited

OTHER PUBLICATIONS

International Search Report dated Jan. 29, 2013 in International (PCT) Application No. PCT/JP2012/080769.
International Preliminary Report on Patentability and Written Opinion dated Jun. 3, 2014 in International (PCT) Application No. PCT/JP2012/080769.
Extended European Search Report dated Apr. 1, 2015 in European Application No. 12852725.6.
Byrn et al., "Hydrates & Solvates", Solid-State Chemistry of Drugs, Chapter 11, 1999, pp. 233-247.
Morissette et al., "High-throughput crystallization: polymorphs, salts, co-crystals and solvates of pharmaceutical solids", Advanced Drug Delivery Reviews, vol. 56, 2004, pp. 275-300.
Rouhi et al., "The Right Stuff", Science & Technology, vol. 81, No. 8, Feb. 24, 2003, pp. 32-35.
Banker et al., "Modern Pharmaceutics", Marcel Dekker, Inc., 3rd edition, 1996, 3 pages.
NIH: National Cancer Institute, Lymphoma—Patient Version, 2015, Web <http://www.cancer.gov/types/lymphoma>.
Healthline, Non-Hodgkin's Lymphoma. 2015, Web <http://www.healthline.com/health/non-hodgkins-lymphoma#ReadThisNext0>.
Office Action dated Dec. 17, 2015 in U.S. Appl. No. 14/666,496.
Burger et al., "Safety and activity of ibrutinib plus rituximab for patients with high-risk chronic lymphocytic leukaemia: a single-arm, phase 2 study", Lancet Oncology, vol. 15, No. 10, Aug. 2014, pp. 1090-1099.
Damle et al., "Abstract 3531: Changes in immune cell populations in relapsed/refractory CLL patients treated with a Bruton's Tyrosine Kinase (BTK) Inhibitor, Ibrutinib (PCI-32765), in combination with Bendamustine and Rituximab (BR)", Cancer Research, vol. 73, No. 8, Suppl. 1, Apr. 2013, p. 3531
Hoellenriegel et al., "In Vivo Inhibition of BCR Activation in High-Risk CLL Patients On Therapy with Bruton's Tyrosine Kinase Inhibitor Ibrutinib: Correlative Studies from an Ongoing Phase 2 Clinical Trial", Blood, vol. 120, No. 21, 2012, p. 186.
Burger et al., "The Btk Inhibitor Ibrutinib (PCI-32765) in Combination with Rituximab Is Well Tolerated and Displays Profound Activity in High-Risk Chronic Lymphocytic Leukemia (CLL) Patients", Blood, vol. 120, No. 21, 2012, p. 187.
Herter et al., "Preclinical Activity of the Type II CD20 Antibody GA101 (Obinutuzumab) Compared with Rituximab and Ofaturnumab In Vitro and in Xeno graft Models", Molecular Cancer Therapeutics, vol. 12, No. 10, Oct. 2013, pp. 2031-2042.
Golay et al., "Glycoengineered CD20 antibody obinutuzumab activates neutrophils and mediates phagocytosis through CD16B more efficiently than rituximab", Blood, vol. 122, No. 20, Nov. 2013, pp. 3482-3491.
Sehn et al., "Randomized Phase II Trial Comparing GA101 (Obinutuzumab) with Rituximab in Patients with Relapsed CD20 Indolent B-Cell Non-Hodgkin Lymphoma: Preliminary Analysis of the GAUSS Study", Blood, vol. 118, No. 20, 2011, p. 269.
International Search Report and Written Opinion dated Jun. 12, 2015 in International Application No. PCT/EP2014/073640.
International Search Report and Written Opinion dated Jun. 30, 2015 in corresponding International Application No. PCT/JP2015/001676.
Simon Rule et al., "A Phase I Study of the Oral Btk Inhibitor ONO-4059 In Patients with Relapsed/Refractory B-Cell Lymphoma", Blood Journal, 2013, vol. 122, Issue 21, p. 4397, Abstract #676.
Ryohei Kozaki et al., "Development of a Bruton's Tyrosine Kinase (Btk) inhibitor—ONO-WG-307, a potential treatment for B-cell malignancies", Cancer Research, 2012, vol. 72, No. 8, Supp. 1, Abstract # 857.
R. Eric Davis et al., "Chronic active B-cell-receptor signaling in diffuse large B-cell lymphoma", Nature, 2010, vol. 463, pp. 88-92.
Kozaki et al., "Kinome Reprogramming in DLBCL by the BTK-Specific Inhibitor ONO-4059 Highlights Synergistic Combinations for Clinical Application", haematologica, Jun. 2014, vol. 99, No. Suppl. 1, pp. 137-138.
Lannutti et al., "CAL-101, a Specific Inhibitor of the P110DELTA Isoform of Phosphatidylinositide 3-Kinase, for the Treatment of Non-Hodgkins Lymphomas", haematologica, Jun. 2009, vol. 94, No. Suppl. 2, pp. 272-273.
Yang, "Idelalisib: First-in-Class PI3K Delta Inhibitor for the Treatment of Chronic Lymphocytic Leukemia, Small Lymphocytic Leukemia, and Follicular Lymphoma", Clinical Cancer Research, vol. 21, No. 7, Apr. 2015, pp. 1537-1542.
Tannheimer, "Combination of Idelalisib and ONO/GS-4059 in Lymphoma Cell Lines Sensitive and Resistant to BTK Inhibitors", Blood Journal, vol. 126, issue 23, Dec. 2015, p. 3697.
International Search Report dated Jan. 11, 2016 in International (PCT) Application No. PCT/US2016/038763.
Anderson, "The process of structure-based drug design," Chemistry and Biology, vol. 10, Issue 9, Sep. 2003, pp. 787-797.
Stella et al., "Prodrug strategies to overcome poor water solubility," Advanced Drug Delivery Reviews 59 (2007) 677-694.
Written Opinion dated Apr. 4, 2017 in Singapore Application No. 11201603613Y.
Office Action dated Aug. 11, 2017 in Korean Application No. 10-2016-7014779, with English Translation.
Byrd et al., "The Btk Inhibitor Ibrutinib (PCI-32765) Alone and in Combination with Rituximab for CLL or SLL", 5 Minute Journal Club (POST-ASH) Issue 2 (2013), 15 pages.
Waghmare et al., "Propylphosphonic Anhydride (T3P®): An Expedient Reagent for Organic Synthesis", Review Journal of Chemistry, 4(2):53-131 (2014).
Meadows et al., "PI3Kδ inhibitor, GS-1101 (CAL-101), attenuates pathway signaling, induces apoptosis, and overcomes signals from the microenvironment in cellular models of Hodgkin lymphoma", Blood, vol. 119, No. 8, Feb. 23, 2012, pp. 1897-1900.

PURINONE DERIVATIVE

TECHNICAL FIELD

The present invention relates to compounds represented by general formula (I)

[C1]

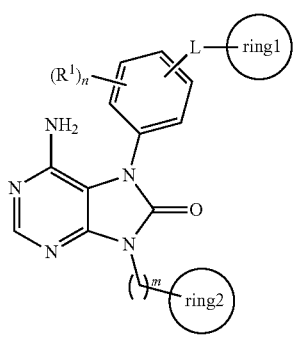

(I)

(all of the symbols in the formula have the same definitions as given below), optical isomers thereof or their mixture, salts thereof, solvates thereof, N-oxides thereof, and prodrugs thereof (abbreviated below as "compounds of the present invention").

BACKGROUND ART

Bruton's tyrosine kinase (abbreviated below as "Btk") belongs to the Tec family of kinases, which are non-receptor tyrosine kinases, and is selectively expressed in the B cell and myelocyte lines. Btk plays an important role in signal transduction in B cells and is a factor that contributes to the survival, differentiation, proliferation, and activation of B cells. Signaling in B cells via the B cell antigen receptor (BCR) induces a broad range of biological responses, and abnormal signal transduction here causes abnormal B cell activation and the formation of pathogenic autoantibodies. Btk is believed to form a link in the BCR-mediated signal transduction pathways into B cells. Thus, X-linked agammaglobulinemia (XLA) is known to be caused by a defect in the human Btk gene that results in the induction of abnormal B cell differentiation and a drastic decline in immunoglobulin production (refer to Non-patent Document 1). The symptoms of this disease include a substantial decline in B cells in the peripheral blood and an increased susceptibility to bacterial infections. Btk is also known to participate in mast cell activation and in the physiological functions of platelets. Due to this, compounds that have a Btk inhibitory activity are effective for the treatment of diseases in which B cells or mast cells participate, for example, allergic diseases, autoimmune diseases, inflammatory diseases, thromboembolic diseases, and cancers (refer to Non-patent Document 2).

The following compounds are known as prior art for the compounds of the present invention.

Compounds represented by general formula (A) are known as compounds that have a Btk inhibitory activity

[C2]

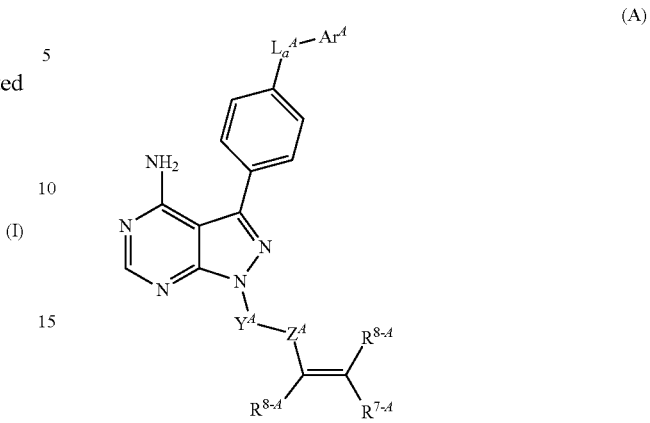

(in the formula, $L_a^A$ represents $CH_2$, O, NH, or S; $Ar^A$ represents substituted or unsubstituted aryl or substituted or unsubstituted heteroaryl; $Y^A$ represents any substituent selected from alkyl, heteroalkyl, cycloalkyl, heterocycloalkyl, aryl, and heteroaryl; $Z^A$ represents CO, OCO, NHCO, or CS; $R^{7-A}$ and $R^{8-A}$ each independently represent H, unsubstituted $C_1$-$C_4$ alkyl, substituted $C_1$-$C_4$ alkyl, unsubstituted $C_1$-$C_4$ heteroalkyl, substituted $C_1$-$C_4$ heteroalkyl, unsubstituted $C_3$-$C_6$ cycloalkyl, substituted $C_3$-$C_6$ cycloalkyl, unsubstituted $C_2$-$C_6$ heterocycloalkyl, and substituted $C_2$-$C_6$ heterocycloalkyl; or $R^{7-A}$ and $R^{8-A}$ together form a bond; and $R^{6-A}$ represents H, substituted or unsubstituted $C_1$-$C_4$ alkyl, substituted or unsubstituted $C_1$-$C_4$ heteroalkyl, $C_1$-$C_6$ alkoxyalkyl, $C_1$-$C_8$ alkylaminoalkyl, substituted or unsubstituted $C_3$-$C_6$ cycloalkyl, or substituted or unsubstituted aryl (the definitions of these groups have been excerpted))(refer to Patent Documents 1, 2, and 3).

On the other hand, for example, compounds represented by general formula (B)

[C3]

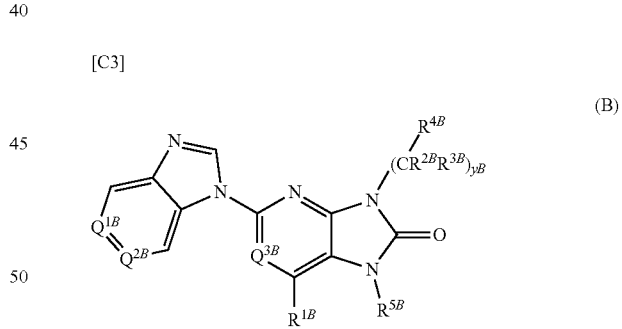

(in the formula, $Q^{1B}$ and $Q^{2B}$ are independently selected from $CX^{1B}$, $CX^{2B}$, and nitrogen; $Q^{3B}$ represents N or CH; $X^{1B}$ and $X^{2B}$ are independently selected from the group consisting of hydrogen, ($C_1$-$C_6$) alkyl, cyano, halogen, and so forth; $R^{1B}$ is selected from the group consisting of hydrogen and ($C_1$-$C_6$) alkyl; yB represents 0 or an integer from 1 to 3; $R^{2B}$ and $R^{3B}$ are independently selected from hydrogen and ($C_1$-$C_6$) alkyl; $R^{4B}$ is selected from the group consisting of alkyl, heterocyclyl, aryl, heteroaryl, and so forth; and $R^{5B}$ is selected from the group consisting of alkyl, heterocyclyl, and substituted heterocyclyl (the definitions of these groups have been excerpted)) (refer to Patent Document 4) are known as compounds that have a purinone skeleton.

Compounds represented by general formula (C) are also known

[C4]

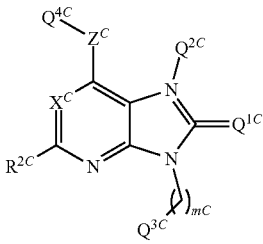

(in the formula, $X^C$ is selected from the group consisting of nitrogen and $CR^{8C}$; $R^{8C}$ is selected from the group consisting of hydrogen, halogen, substituted or unsubstituted alkyl, and so forth; $Q^{1C}$ is selected from the group consisting of O, S, and so forth; $Z^C$ is selected from the group consisting of oxygen, sulfur, and $NY^{5C}$; $Y^{5C}$ is selected from the group consisting of hydrogen, substituted or unsubstituted alkyl, and so forth; $Q^{2C}$, $Q^{3C}$, and $Q^{4C}$ are independently selected from the group consisting of hydrogen, substituted or unsubstituted alkyl, substituted or unsubstituted aryl, and so forth; $R^{2C}$ is selected from the group consisting of hydrogen and substituted or unsubstituted alkyl; and nC represents 0, 1, 2, 3, or 4 (the definitions of these groups have been excerpted)) (refer to Patent Document 5).

Compounds having a purinone skeleton are also disclosed as formula 20 (refer to paragraph number 0028) in Patent Document 6.

Compounds represented by general formula (D) are also known

[C5]

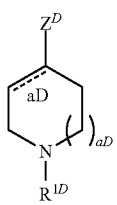

(in the formula, $R^{1D}$ represents a group selected from hydrogen, substituted or unsubstituted alkyl,

[C6]

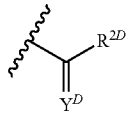

and so forth; $R^{2D}$ represents substituted or unsubstituted alkyl, substituted or unsubstituted alkenyl, or substituted or unsubstituted alkynyl; $Y^D$ represents a group selected from O, C—NO$_2$, and S; $Z^D$ represents a group selected from

[C 7]

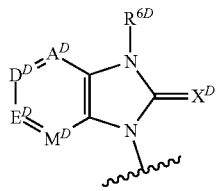

and so forth; here, $A^D$, $D^D$, $E^D$, and $M^D$ each independently represent $CR^{12D}$, N, and N-oxide; $R^{12D}$ represents a group selected from hydrogen, halogen, amino, hydroxy, and cyano; $X^D$ represents a group selected from O, C—NO$_2$, and S; $R^{6D}$ represents a group selected from substituted or unsubstituted cycloalkyl, substituted or unsubstituted heteroalkyl, and substituted or unsubstituted aryl; the indication aD represented by the dashed line represents a single bond or a double bond; and nD represents an integer selected from 0, 1, and 2) (refer to Patent Document 7).

The compounds of the present invention are compounds that, in addition to having a Btk-selective inhibitory activity, exhibit an excellent metabolic stability and can avoid a CYP inhibitory activity and adverse reactions such as, for example, hepatotoxicity; however, there is no statement or suggestion relating to these characteristic features in any of the prior art documents.

Patent Document 1: Japanese Translation of PCT Application No. 2010-504324

Patent Document 2: WO 2008/121742

Patent Document 3: WO 2010/009342

Patent Document 4: WO 2008/060301

Patent Document 5: WO 2007/142755

Patent Document 6: Japanese Translation of PCT Application No. 2003-509427

Patent Document 7: WO 2003/037890

Non-patent Document 1: Nature, Volume 361, pp. 226-233, 1993

Non-patent Document 2: *Anticancer Agents in Medicinal Chemistry*, Volume 7, Number 6, pp. 624-632, 2007

DISCLOSURE OF THE INVENTION

In order to provide a very safe therapeutic agent for diseases in which B cells and/or mast cells participate, an object of the present invention is to develop a compound that, in addition to having a Btk-selective inhibitory activity, exhibits an excellent metabolic stability and can avoid hepatotoxicity or the like.

In order to achieve the above object, the present inventors carried out intensive investigations directed to discover compounds having a Btk-selective inhibitory activity and discovered the compounds of the present invention as a result. Moreover, it was also discovered that these compounds are compounds that exhibit an excellent metabolic activity and can avoid hepatotoxicity or the like, and the present invention was achieved as a result.

That is, the present invention relates to
[1] a compound represented by general formula (I)

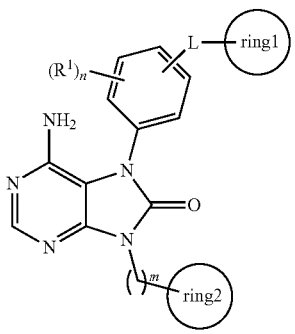

(I)

(in the formula,
L represents (1) —O—, (2) —S—, (3) —SO—, (4) —SO$_2$— (5) —NH—, (6) —C(O)—, (7) —CH$_2$—O—, (8) —O—CH$_2$—, (9) —CH$_2$—, or (10) —CH(OH)—;
$R^1$ represents (1) a halogen atom, (2) a $C_{1-4}$ alkyl group, (3) a $C_{1-4}$ alkoxy group, (4) a $C_{1-4}$ haloalkyl group, or (5) a $C_{1-4}$ haloalkoxy group;
ring1 represents a 4- to 7-membered cyclic group, which may be substituted by from one to five substituents each independently selected from the group consisting of (1) halogen atoms, (2) $C_{1-4}$ alkyl groups, (3) $C_{1-4}$ alkoxy groups, (4) nitrile, (5) $C_{1-4}$ haloalkyl groups, and (6) $C_{1-4}$ haloalkoxy groups, wherein when two or more substituents are present on ring1, these substituents may form a 4- to 7-membered cyclic group together with the atoms in ring1 to which these substituents are bound;
ring2 represents a 4- to 7-membered saturated heterocycle, which may be substituted by from one to three —K—$R^2$;
K represents (1) a bond, (2) a $C_{1-4}$ alkylene, (3) —C(O)—, (4) —C(O)—CH$_2$—, (5) —CH$_2$—C(O)—, (6) —C(O)O—, or (7) —SO$_2$— (wherein the bond on the left is bound to the ring2);
$R^2$ represents (1) a $C_{1-4}$ alkyl, (2) a $C_{2-4}$ alkenyl, or (3) a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;
$R^3$ and $R^4$ each independently represent (1) a hydrogen atom, or (2) a $C_{1-4}$ alkyl group which may be substituted by $OR^9$ or $CONR^{10}R^{11}$;
$R^3$ and $R^4$ may, together with the nitrogen atom to which they are bound, form a 4- to 7-membered nitrogenous saturated heterocycle, which may be substituted by an oxo group or a hydroxyl group;
$R^5$ and $R^6$ each independently represent (1) a hydrogen atom, (2) a $C_{1-4}$ alkyl group, or (3) a phenyl group;
$R^7$ represents (1) a hydrogen atom or (2) a $C_{1-4}$ alkyl group;
$R^8$ represents (1) a hydrogen atom, (2) a $C_{1-4}$ alkyl group, (3) a phenyl group, or (4) a benzotriazolyl group;
$R^9$ represents (1) a hydrogen atom or (2) a $C_{1-4}$ alkyl group;
$R^{10}$ and $R^{11}$ each independently represent (1) a hydrogen atom or (2) a $C_{1-4}$ alkyl group;
n represents an integer from 0 to 4;
m represents an integer from 0 to 2; and
when n is two or more, the $R^1$'s may be the same as each other or may differ from one another), an optical isomer thereof or their mixture, a salt thereof, a solvate thereof, an N-oxide thereof, or a prodrug thereof;
[2] the compound according to [1] above, wherein $R^2$ is a $C_{2-4}$ alkenyl group or a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;
[3] the compound according to [1] above, wherein ring1 is a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, and (5) $CF_3$;
[4] the compound according to [1] above, wherein ring2 is a 4- to 7-membered nitrogenous saturated heterocycle, which may be substituted by from one to three —K—$R^2$;
[5] the compound according to [4] above, wherein the 4- to 7-membered nitrogenous saturated heterocycle is an azetidine, pyrrolidine, or piperidine ring;
[6] the compound according to [1] above, represented by general formula (I-1)

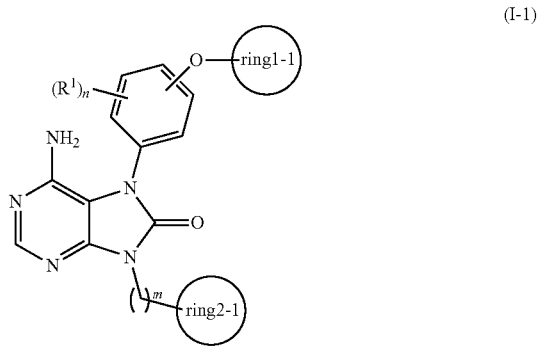

(I-1)

(in the formula, ring1-1 represents a benzene, cyclohexane, or pyridine ring, each of which may be substituted by from one to five substituents each independently selected from the group consisting of (1) halogen atoms, (2) $C_{1-4}$ alkyl groups, (3) $C_{1-4}$ alkoxy groups, (4) nitrile, and (5) $CF_3$, and ring2-1 represents a 4- to 7-membered nitrogenous saturated heterocycle, which may be substituted by from one to three —K—$R^2$, wherein the other symbols have the same definitions as above);
[7] the compound according to [6] above, wherein $R^2$ is a $C_{2-4}$ alkenyl group or a $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$;
[8] the compound according to [1] above, which is (1) 9-(1-acryloyl-3-azetidinyl)-6-amino-7-(4-phenoxyphenyl)-7,9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{

(3R)-1-[(2E)-4-(dimethylamino)-2-butenoyl]-3-pyrrolidinyl}-7,9-dihydro-8H-purin-8-one, (7) 6-amino-9-[1-(2-butynoyl)-3-pyrrolidinyl]-7-(4-phenoxyphenyl)-7,9-dihydro-8H-purin-8-one, or (8) 6-amino-9-{1-[(2E)-4-(dimethylamino)-2-butenoyl]-3-pyrrolidinyl}-7-(4-phenoxyphenyl)-7,9-dihydro-8H-purin-8-one, or an optical isomer thereof or their mixture;

[9] a pharmaceutical composition comprising a compound represented by general formula (I) according to [1] above, an optical isomer thereof or their mixture, a salt thereof, a solvate thereof, an N-oxide thereof, or a prodrug thereof;

[10] the pharmaceutical composition according to [9] above, that is a Btk inhibitor;

[11] the pharmaceutical composition according to [9] above, that is a prophylactic agent and/or a therapeutic agent for a Btk-related disease;

[12] the pharmaceutical composition according to [11] above, wherein the Btk-related disease is an allergic disease, an autoimmune disease, an inflammatory disease, a thromboembolic disease, or a cancer;

[13] the pharmaceutical composition according to [12] above, wherein the cancer is a non-Hodgkin's lymphoma;

[14] the pharmaceutical composition according to [9] above, which is an inhibitor of B-cell activation;

[15] a method of preventing and/or treating a Btk-related disease, comprising administering to a mammal of an effective amount of a compound represented by general formula (I) according to [1] above, an optical isomer thereof or their mixture, a salt thereof, a solvate thereof, an N-oxide thereof, or a prodrug thereof;

[16] a compound represented by general formula (I) according to [1] above, an optical isomer thereof or their mixture, a salt thereof, a solvate thereof, an N-oxide thereof, or a prodrug thereof, for preventing and/or treating a Btk-related disease; and

[17] use of a compound represented by general formula (I) according to [1] above, an optical isomer thereof or their mixture, a salt thereof, a solvate thereof, an N-oxide thereof, or a prodrug thereof, to produce an agent for preventing and/or treating a Btk-related disease.

The compounds of the present invention, in addition to having a Btk-selective inhibitory activity, exhibit an excellent metabolic stability and can avoid hepatotoxicity or the like, and as a consequence are useful as very safe therapeutic agents for diseases in which B cells and/or mast cells participate, such as non-Hodgkin's lymphoma.

BEST MODE FOR CARRYING OUT THE INVENTION

The present invention is described in detail below.

In the present invention, "having a Btk-selective inhibitory activity" denotes having a Btk-selective inhibitory activity with respect to non-Btk tyrosine kinases and particularly lymphocyte-specific protein tyrosine kinase (Lck), protein-tyrosine kinase fyn (Fyn), and v-yes-1 Yamaguchi sarcoma viral-related oncogene homolog isoform A (LynA). This property makes it possible to avoid unpredictable adverse reactions caused by the inhibition of other tyrosine kinases. For example, the appearance of retinal abnormalities is known in Lck-deficient mice (Oncogene, Volume 16, pp. 2351-2356, 1998), which raises the possibility that adverse reactions will be caused in the eye in the event of an inhibition of Lck.

In the present invention, the halogen atom denotes fluorine, chlorine, bromine, and iodine.

In the present invention, the $C_{1-4}$ alkyl group denotes straight-chain and branched-chain $C_{1-4}$ alkyl groups, e.g., methyl, ethyl, propyl, isopropyl, butyl, sec-butyl, and tert-butyl.

In the present invention, the $C_{1-4}$ alkylene group denotes methylene, ethylene, propylene, butylene, and their isomers.

In the present invention, the $C_{1-4}$ alkoxy group denotes straight-chain and branched-chain $C_{1-4}$ alkoxy groups, e.g., methoxy, ethoxy, propoxy, isopropoxy, butoxy, isobutyloxy, and tert-butoxy.

In the present invention, the $C_{2-4}$ alkenyl group denotes straight-chain and branched-chain $C_{2-4}$ alkenyl groups, e.g., ethenyl, 1-propenyl, 2-propenyl, 1-butenyl, 2-butenyl, 3-butenyl, and 1,3-butadienyl.

In the present invention, the $C_{2-4}$ alkynyl group denotes straight-chain and branched-chain $C_{2-4}$ alkynyl groups, e.g., ethynyl, 1-propynyl, 2-propynyl, 1-butynyl, 2-butynyl, 3-butynyl, and 1,3-butadiynyl.

In the present invention, the $C_{1-4}$ haloalkyl group denotes a group provided by substituting one or two or more halogen atoms into a $C_{1-4}$ alkyl group, and can be exemplified by a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, and a 4-bromobutyl group.

In the present invention, the $C_{1-4}$ haloalkoxy group denotes a group provided by substituting one or two or more halogen atoms into a $C_{1-4}$ alkoxy group, and can be exemplified by a trifluoromethoxy group, a trichloromethoxy group, a chloromethoxy group, a bromomethoxy group, a fluoromethoxy group, an iodomethoxy group, a difluoromethoxy group, a dibromomethoxy group, a 2-chloroethoxy group, a 2,2,2-trifluoroethoxy group, a 2,2,2-trichloroethoxy group, a 3-bromopropoxy group, a 3-chloropropoxy group, a 2,3-dichloropropoxy group, a 1-fluorobutoxy group, a 4-fluorobutoxy group, and a 1-chlorobutoxy group.

In the present invention, the 4- to 7-membered cyclic group denotes a $C_{4-7}$ carbocyclic ring or a 4- to 7-membered heterocycle.

In the present invention, the $C_{4-7}$ carbocyclic ring denotes a $C_{4-7}$ monocyclic aliphatic or aromatic carbocyclic ring. The aliphatic system may be partially or completely saturated. Examples here are cyclobutane, cyclopentane, cyclohexane, cycloheptane, cyclopentene, cyclohexene, cycloheptene, cyclobutadiene, cyclopentadiene, cyclohexadiene, cycloheptadiene, and benzene.

In the present invention, the $C_{5-6}$ carbocyclic ring denotes a $C_{5-6}$ monocyclic aliphatic or aromatic carbocyclic ring. The aliphatic system may be partially or completely saturated. Examples here are cyclopentane, cyclohexane, cyclopentene, cyclohexene, cyclopentadiene, cyclohexadiene, and benzene.

In the present invention, the 4- to 7-membered heterocycle denotes a 4- to 7-membered unsaturated heterocycle or a 4- to 7-membered saturated heterocycle.

In the present invention, the 4- to 7-membered unsaturated heterocycle denotes an unsaturated 4- to 7-membered monocyclic heterocycle that contains from one to five hetero atoms selected from the oxygen atom, nitrogen atom, and sulfur atom, and can be exemplified by pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, and thiadiazepine.

In the present invention, the 4- to 7-membered saturated heterocycle denotes a partially or completely saturated 4- to 7-membered monocyclic heterocycle that contains from one to five hetero atoms each independently selected from the oxygen atom, nitrogen atom, and sulfur atom, and can be exemplified by azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetane, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, and dithiane.

In the present invention, the 4- to 7-membered nitrogenous saturated heterocycle refers to those 4- to 7-membered saturated heterocycles that necessarily contain at least one nitrogen atom. Examples are azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, and thiomorpholine.

The 4- to 6-membered nitrogenous saturated heterocycles can be exemplified in the present invention by azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, and thiomorpholine.

L in the present invention is preferably —O—, —CH$_2$—O—, —O—CH$_2$—, —NH—, —C(O)—, —CH$_2$—, or —CH(OH)—.

R$^1$ in the present invention is preferably a halogen atom or a C$_{1-4}$ alkoxy group.

The 4- to 7-membered cyclic group for ring1 in the present invention is preferably a C$_{5-6}$ carbocyclic ring or a 4- to 7-membered unsaturated heterocycle and is more preferably a benzene, cyclohexane, or pyridine ring.

The 4- to 7-membered saturated heterocycle for ring2 in the present invention is preferably a 4- to 7-membered nitrogenous saturated heterocycle, is more preferably a 4- to 6-membered nitrogenous saturated heterocycle, is even more preferably an azetidine, pyrrolidine, or piperidine ring, and particularly preferably is an azetidine or pyrrolidine ring.

K in the present invention is preferably a bond or —C(O)—.

R$^2$ in the present invention is preferably a C$_{2-4}$ alkenyl group or a C$_{2-4}$ alkynyl group, each of which may be substituted by from one to five substituents each independently selected from the group consisting of (1) NR$^3$R$^4$, (2) halogen atoms, (3) CONR$^5$R$^6$, (4) CO$_2$R$^7$, and (5) OR$^8$.

m in the present invention is preferably 0 or 1 and more preferably is 0.

Any combination of the individual preferred groups provided as examples above and selected from L, R$^1$, ring1, ring2, K, R$^2$, and m is also preferred in the present invention.

Compounds represented by general formula (I-1)

[C10]

(I-1)

(all of the symbols in the formula have the same definitions as above) are preferred in the present invention among compounds with general formula (I).

R$^1$ in general formula (I-1) is preferably a halogen atom or a C$_{1-4}$ alkoxy group.

The ring1-1 in general formula (I-1) is preferably a benzene ring.

The 4- to 7-membered nitrogenous saturated heterocycle for ring2-1 in general formula (I-1) is preferably an azetidine, pyrrolidine, or piperidine ring and more preferably is an azetidine or pyrrolidine ring.

With regard to the —K—$R^2$— substituent on the ring2-1 in general formula (I-1), K is preferably a bond or —C(O)— and $R^2$ is preferably a $C_{2-4}$ alkenyl group or $C_{2-4}$ alkynyl group, each of which may be substituted by from one to five substituents each independently selected from the group consisting of (1) $NR^3R^4$, (2) halogen atoms, (3) $CONR^5R^6$, (4) $CO_2R^7$, and (5) $OR^8$.

m in general formula (I-1) is preferably 0 or 1 and more preferably is 0.

Any combination of the individual preferred groups provided as examples above is also preferred for general formula (I-1).

[Isomers]

The present invention encompasses all isomers, unless specifically indicated otherwise. For example, the alkyl groups include both straight-chain alkyl groups and branched-chain alkyl groups. Moreover, all of the following are included in the present invention: geometric isomers (E configuration, Z configuration, cis configuration, trans configuration) for double bonds, rings, and condensed rings; optical isomers due to, for example, the presence of an asymmetric carbon atom (R and S configurations, α and β positions, enantiomers, diastereomers); optically active forms that exhibit optical rotation (D, L, d, and l configurations); polar forms generated by chromatographic separation (high-polarity forms, low-polarity forms); equilibrium compounds; rotational isomers; mixtures of the preceding in any proportions; and racemic mixtures. The present invention also encompasses all isomers arising due to tautomers.

In addition, an optical isomer in the present invention refers not only to the 100% pure optical isomer, but may also include another optical isomer at less than 50%.

In the present invention, unless specifically stated otherwise, and as is clear to the individual skilled in the art, the

[C 11] 

symbol represents bonding toward the back side of the plane of the paper (that is, the α-position); the

[C 12] 

symbol represents bonding toward the front side of the plane of the paper (that is, the β-position); and

[C 13] 

represents the α-position, β-position, or their mixture in any proportion.

The compounds represented by general formula (I) are converted into the corresponding salts by known methods. The salt is preferably a water-soluble salt. Suitable salts can be exemplified by the salts with alkali metals (potassium, sodium, and so forth), salts with alkaline-earth metals (calcium, magnesium, and so forth), the ammonium salt, salts with pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and so forth), and acid addition salts (inorganic acid salts (the hydrochloride, hydrobromide, hydroiodide, sulfate, phosphate, nitrate, and so forth) and organic acid salts (the acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, and so forth)).

The compounds represented by general formula (I) and their salts can also be converted into solvates. This solvate preferably is water soluble and has a low toxicity. Suitable solvates can be exemplified by solvates with, for example, water or an alcohol solvent (for example, ethanol).

A prodrug of a compound represented by general formula (I) denotes a compound that is converted by a reaction in vivo, e.g., by an enzyme or gastric acid, into the compound represented by general formula (I). Prodrugs of the compounds with general formula (I) can be exemplified by compounds in which—when the compound represented by general formula (I) has a hydroxyl group—this hydroxyl group is acylated, alkylated, phosphated, or borated (for example, compounds provided by the acetylation, palmitoylation, propanoylation, pivaloylation, succinylation, fumarylation, alanylation, or dimethylaminomethylcarbonylation of the hydroxyl group in the compounds of the invention); other examples are compounds provided by the esterification or amidation of a carboxyl group in a compound represented by general formula (I) (for example, compounds provided by the ethyl esterification, isopropyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of a carboxyl group in a compound represented by general formula (I)). These compounds can be prepared by known methods. In addition, the prodrug of a compound represented by general formula (I) may be a hydrate or anhydrous. The prodrug of a compound represented by general formula (I) is converted under physiological conditions into the compound represented by general formula (I), as described on pages 163 to 198 of Molecular Design in Volume 7 of Development of Medicines (Hirokawa Shoten Co., 1990). In addition, the compounds represented by general formula (I) may be labeled with an isotope (for example, $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, and $^{125}I$)

[Methods for Producing the Compounds of the Present Invention]

The compounds of the present invention can be produced by suitably modifying and combining known methods, for example, the methods described in *Comprehensive Organic Transformations: A Guide to Functional Group Preparations,* 2nd Edition (Richard C. Larock, John Wiley & Sons Inc., 1999), or the methods given in the examples.

Among the compounds represented by general formula (I), compounds in which the ring2 is an unsubstituted 4- to 7-membered nitrogenous saturated heterocycle, i.e., compounds represented by general formula (I-A)

[C14]
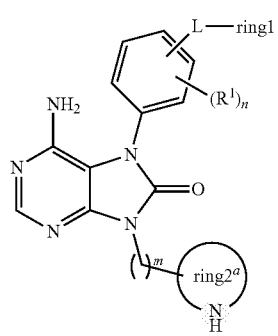
(I-A)
(in the formula, ring2$^a$ represents an unsubstituted 4- to 7-membered nitrogenous saturated heterocycle, while the other symbols have the same definitions as above), can be produced using the following reaction scheme 1.
Reaction scheme 1
[C 15]
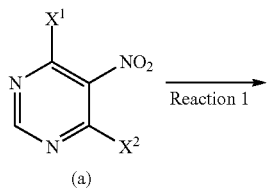
(a)
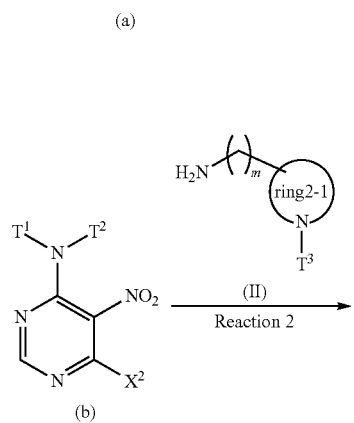
(b)
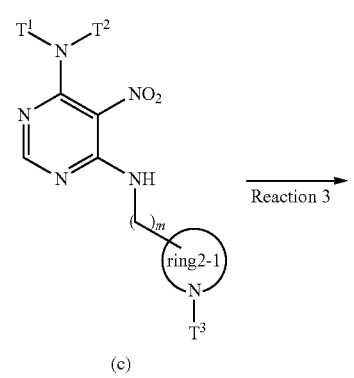
(c)
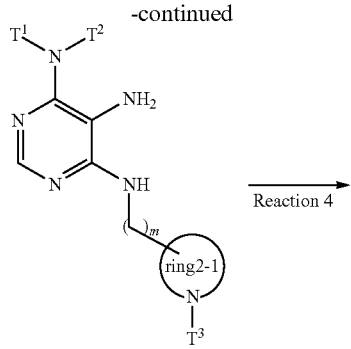
(d)
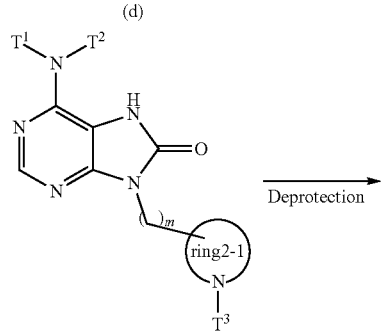
(e)
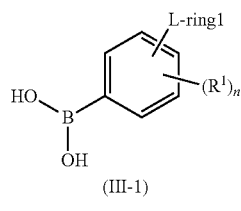
(III-1)
or
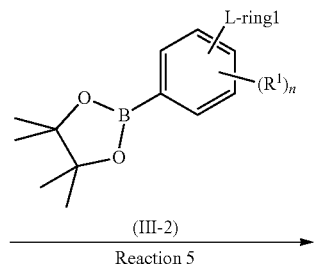
(III-2)
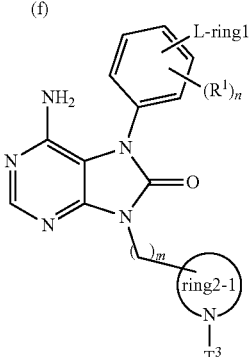
(f)
(g)

-continued

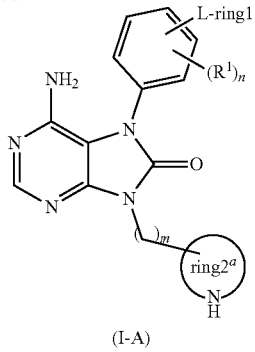

(I-A)

(In the formulas, $T^1$ and $T^2$ each independently represent a protective group for the amino group (for example, the benzyl (Bn) group, 4-methoxybenzyl group, and 3,4-dimethoxybenzyl group); $X^1$ and $X^2$ each independently represent a halogen atom; ring2-1 represents a ring2$^a$ that has been protected by a protective group represented by $T^3$ (for example, the tert-butoxycarbonyl (Boc) group and benzyloxycarbonyl (Cbz) group); and the other symbols have the same definitions as above.)

The reaction 1 in reaction scheme 1 is known and is carried out using a compound with general formula (a) and a protected amine derivative, i.e., a compound represented by $T^1T^2$-NH ($T^1$ and $T^2$ in the formula have the same definitions as above) and running the reaction in an organic solvent (for example, dichloromethane, tetrahydrofuran, dioxane, dimethylformamide, dimethylacetamide, and 1-methyl-2-pyrrolidone) in the presence of a base (for example, triethylamine, N,N-diisopropylethylamine, pyridine, 4-dimethylaminopyridine, and N-methylmorpholine) at a temperature from −20° C. to room temperature.

The reaction 2 in reaction scheme 1 is known and is carried out using a compound with general formula (b) and a compound represented by general formula (II) and running the reaction in an organic solvent (for example, dioxane, acetonitrile, tetrahydrofuran, dimethylformamide, dimethylacetamide, and 1-methyl-2-pyrrolidone) in the presence of a base (for example, triethylamine, N,N-diisopropylethylamine, pyridine, 4-dimethylaminopyridine, and N-methylmorpholine) at a temperature from −20° C. to 70° C.

The reaction 3 in reaction scheme 1 is known and is carried out using a compound represented by general formula (c) and using a metal reagent (for example, zinc, iron, tin, tin chloride, iron chloride, samarium, indium, and sodium borohydride-nickel chloride) in a water-miscible solvent (for example, ethanol, methanol, tetrahydrofuran, and ethyl acetate) in the presence or absence of an acid (for example, hydrochloric acid, hydrobromic acid, ammonium chloride, acetic acid, and ammonium formate) at a temperature of 0° C. to 150° C.

The reaction 4 in reaction scheme 1 is known and is carried out using a compound represented by general formula (d) and using a reagent (for example, 1,1'-carbonyldiimidazole (CDI) and triphosgene) in an organic solvent (for example, tetrahydrofuran, dimethylformamide, and dimethylacetamide) in the presence or absence of a base (for example, triethylamine, N,N-diisopropylethylamine, pyridine, 4-dimethylaminopyridine, and N-methylmorpholine) at from a temperature generated by ice cooling to the reflux temperature.

The deprotection reactions for the protective groups in reaction scheme 1 are known and can be run by the methods described below. Examples here are (1) deprotection reactions based on alkaline hydrolysis, (2) deprotection reactions under acidic conditions, (3) deprotection reactions based on hydrogenolysis, (4) deprotection reactions for the silyl group, (5) deprotection reactions using a metal, and (6) deprotection reactions using a metal complex.

These methods are specifically described below.

(1) The deprotection reaction based on alkaline hydrolysis may be carried out, for example, in an organic solvent (for example, methanol, tetrahydrofuran, and dioxane) at from 0° C. to 40° C. using an alkali metal hydroxide (for example, sodium hydroxide, potassium hydroxide, and lithium hydroxide), an alkaline-earth metal hydroxide (for example, barium hydroxide and calcium hydroxide), or a carbonate (for example, sodium carbonate and potassium carbonate), or an aqueous solution of the preceding, or their mixture.

(2) The deprotection reaction under acidic reactions may be carried out, for example, at from 0° C. to 100° C. in the presence or absence of 2,2,2-trifluoroethanol, in an organic solvent (for example, dichloromethane, chloroform, dioxane, ethyl acetate, methanol, isopropyl alcohol, tetrahydrofuran, and anisole) and in an organic acid (for example, acetic acid, trifluoroacetic acid, methanesulfonic acid, and p-tosylate) or an inorganic acid (for example, hydrochloric acid and sulfuric acid) or their mixture (for example, hydrogen bromide/acetic acid).

(3) The deprotection reaction based on hydrogenolysis may be carried out, for example, at 0° C. to 200° C. in a solvent (for example, an ether (for example, tetrahydrofuran, dioxane, dimethoxyethane, and diethyl ether), an alcohol (for example, methanol and ethanol), a benzene solvent (for example, benzene and toluene), a ketone (for example, acetone and methyl ethyl ketone), a nitrile (for example, acetonitrile), an amide (for example, N,N-dimethylformamide), water, ethyl acetate, acetic acid, or a mixed solvent of two or more of the preceding) in the presence of a catalyst (for example, palladium-carbon, palladium black, palladium hydroxide-carbon, platinum oxide, and Raney nickel) in a hydrogen atmosphere at normal pressure or elevated pressure or in the presence of ammonium formate.

(4) The deprotection reaction for the silyl group may be carried out, for example, at 0° C. to 40° C. in a water-miscible organic solvent (for example, tetrahydrofuran and acetonitrile) using tetrabutylammonium fluoride. It may also be carried out, for example, at −10° C. to 100° C. in an organic acid (for example, acetic acid, trifluoroacetic acid, methanesulfonic acid, and p-tosylate) or an inorganic acid (for example, hydrochloric acid and sulfuric acid) or their mixture (for example, hydrogen bromide/acetic acid).

(5) The deprotection reaction using a metal may be carried out, for example, at 0° C. to 40° C. in an acidic solvent (for example, acetic acid, a buffer with a pH of 4.2 to 7.2, or a mixed solution of the preceding solutions with an organic solvent such as tetrahydrofuran) in the presence of zinc powder and as necessary while applying ultrasound.

(6) The deprotection reaction using a metal complex may be carried out, for example, at 0° C. to 40° C. in an organic solvent (for example, dichloromethane, N,N-dimethylformamide, tetrahydrofuran, ethyl acetate, acetonitrile, dioxane, and ethanol), water, or their mixed solutions, using a metal complex (for example, tetrakis(triphenylphosphine)palladium(0), bis(triphenylphosphine)palladium(II) dichloride, palladium(II) acetate, and tris(triphenylphosphine)rhodium(I) chloride) in the presence of a trapping reagent (for example, tributyltin hydride, triethylsilane, dimedone, morpholine, diethylamine, and pyrrolidone), an organic acid (for example, acetic acid, formic acid, and 2-ethylhexanoic acid), and/or an organic acid salt (for example, sodium 2-ethylhexanoate and potassium 2-ethylhexanoate) and in the presence or absence of a phosphine-type reagent (for example, triphenylphosphine).

In addition to the preceding, the deprotection reaction may also be carried out using the methods described in, for example, T. W. Greene, *Protective Groups in Organic Synthesis*, Wiley, New York, 1999.

The protective group for an amino group can be exemplified by the benzyloxycarbonyl group, t-butoxycarbonyl group, allyloxycarbonyl (Alloc) group, 1-methyl-1-(4-biphenyl)ethoxycarbonyl (Bpoc) group, trifluoroacetyl group, 9-fluorenylmethoxycarbonyl group, benzyl (Bn) group, p-methoxybenzyl group, benzyloxymethyl (BOM) group, and 2-(trimethylsilyl)ethoxymethyl (SEM) group.

In addition to the preceding, the protective group for an amino group may be any group capable of a facile and selective elimination and is not otherwise particularly limited. For example, the groups described in T. W. Greene, *Protective Groups in Organic Synthesis*, Wiley, New York, 1999, may be used.

The reaction 5 in reaction scheme 1 is known and is carried out using a compound with general formula (f) and a compound represented by general formula (III-1) or general formula (III-2) and running the reaction at from room temperature to 120° C. in an organic solvent (for example, dichloromethane and acetonitrile) in the presence of a base (for example, pyridine, triethylamine, and N,N-diisopropylethylamine), a copper salt (for example, copper(II) acetate), and a drying agent (for example, molecular sieve).

Among compounds with general formula (I), compounds in which ring2 is a 4- to 7-membered nitrogenous saturated heterocycle that is substituted by at least one —K—$R^2$ wherein K represents C(O) and $R^2$ represents a $C_{1-4}$ alkylene or $C_{2-4}$ alkenylene group which may be substituted by halogen, i.e., compounds represented by general formula (I-B)

[C 16]

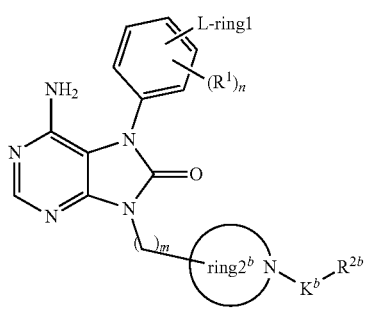

(1-B)

(in the formula, ring2$^b$ represents a 4- to 7-membered nitrogenous saturated heterocycle substituted by —$K^b$—$R^{2b}$; $K^b$ represents —C(O)—; $R^{2b}$ represents a $C_{1-4}$ alkylene or $C_{2-4}$ alkenylene group which may be substituted by halogen; and the other symbols have the same definitions as above), can be produced using a compound with general formula (I-A), which can be produced by reaction scheme 1, and a compound represented by general formula (I-B-1)

[C 17]

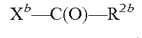   (I-B-1)

(in the formula, $X^b$ represents a halogen atom and $R^{2b}$ has the same definition as above) and carrying out a reaction at a temperature from 0° C. to room temperature in an organic solvent (for example, dichloromethane, chloroform, dimethylformamide, dimethylacetamide, diethyl ether, and tetrahydrofuran) in the presence of a base (for example, triethylamine, pyridine, N,N-diisopropylethylamine, 4-dimethylaminopyridine, and N-methylmorpholine).

Among compounds with general formula (I), compounds in which ring2 is a 4- to 7-membered nitrogenous saturated heterocycle substituted by at least one —K—$R^2$ wherein K represents C(O) and $R^2$ represents a $C_{1-4}$ alkylene or $C_{2-4}$ alkenylene group which may be substituted by $NR^3R^4$, i.e., compounds with general formula (I-C)

[C 18]

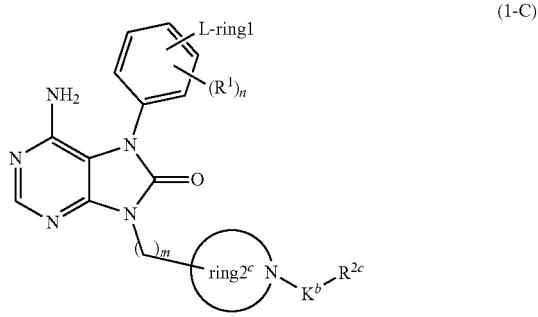

(in the formula, ring2$^c$ represents a 4- to 7-membered nitrogenous saturated heterocycle substituted by —$K^b$—$R^{2c}$; $R^{2c}$ represents a $C_{1-4}$ alkylene or $C_{2-4}$ alkenylene group which may be substituted by $NR^3R^4$; and the other symbols have the same definitions as above), can be produced by reacting a compound represented by general formula (I-C-2)

[C 20]

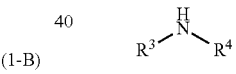

(I-C-2)

(all of the symbols in the formula are defined as above) at from room temperature to 120° C. in an organic solvent (for example, tetrahydrofuran, dioxane, acetonitrile, dimethylformamide, dimethylacetamide, and 1-methyl-2-pyrrolidone) with the compound obtained by reacting a compound represented by general formula (I-A) with a compound represented by general formula (I-C-1)

[C 19]

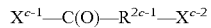   (I-C-1)

$X^{c-1}$—C(O)—$R^{2c-1}$—$X^{c-2}$ (in the formula, $X^{c-1}$ and $X^{c-2}$ each independently represent a halogen atom and $R^{2c-1}$ represents a $C_{1-4}$ alkylene or $C_{2-4}$ alkenylene group) at or below 0° C. in an organic solvent (for example, dichloromethane, chloroform, dimethylformamide, dimethylacetamide, diethyl ether, and tetrahydrofuran) in the presence of a base (for example, triethylamine, pyridine, N,N-diisopropylethylamine, 4-dimethylaminopyridine, and N-methylmorpholine).

Among compounds with general formula (I), compounds in which ring2 is a 4- to 7-membered nitrogenous saturated heterocycle substituted by at least one —K—$R^2$ wherein K represents C(O) and $R^2$ represents a $C_{1-4}$ alkylene, $C_{2-4}$ alkenylene, or $C_{2-4}$ alkynylene group which may be substituted by $CONR^5R^6$, $CO_2R^7$, or $OR^8$, i.e., compounds with general formula (I-D)

[C 21]

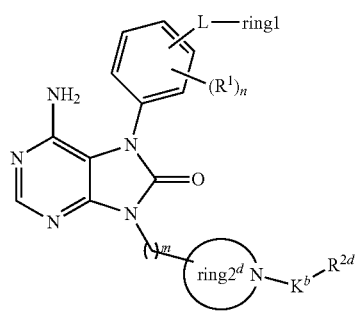

(I-D)

(in the formula, ring$2^d$ represents a 4- to 7-membered nitrogenous saturated heterocycle substituted by at least one —K$^b$—R$^{2d}$; R$^{2d}$ represents a C$_{1-4}$ alkylene, C$_{2-4}$ alkenylene, or C$_{2-4}$ alkynylene group which may be substituted by CONR$^5$R$^6$, CO$_2$R$^7$, or OR$^8$; and the other symbols have the same definitions as above), can be produced using a compound represented by general formula (I-A) and a compound represented by general formula (I-D-1)

[C 22]

$$R^{2d}\text{—CO}_2\text{H} \qquad (\text{I-D-1})$$

(R$^{2d}$ in the formula is defined as above) and carrying out a reaction at from 0° C. to room temperature using a condensing agent (for example, 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, and 1-propanephosphonic acid cyclic anhydride (PPA)) in an organic solvent (for example, chloroform, dichloromethane, dimethylformamide, dimethylacetamide, diethyl ether, and tetrahydrofuran), or without a solvent, in the presence or absence of a base (for example, triethylamine, pyridine, N,N-diisopropylethylamine, 4-dimethylaminopyridine, and N-methylmorpholine) and with or without the use of 1-hydroxybenztriazole (HOBt).

The compounds used as starting materials in each of the reactions in this Description, for example, general formula (a), (II), (III-1), (III-2), (I-B-1), (I-C-1), (I-C-2), and (I-D-1), are either known or can be readily produced by known methods.

For each of the reactions in this Description, the reactions accompanied by the application of heat can be carried out using a water bath, oil bath, sand bath, or microwaves, as will be clear to the individual skilled in the art.

A solid-phase reagent, comprising the reagent carried on a high molecular weight polymer (for example, polystyrene, polyacrylamide, polypropylene, and polyethylene glycol), may be used as appropriate in the reactions in this Description.

The reaction product in each of the reactions of this Description can be purified by the usual purification means, for example, using methods such as distillation at normal pressure or under reduced pressure, high-performance liquid chromatography using silica gel or magnesium silicate, thin-layer chromatography, ion-exchange resins, scavenger resins, column chromatography, washing, recrystallization, and so forth. Purification may be carried out in each reaction or may be performed after the completion of several reactions.

[Toxicity]

The compounds of the present invention have an acceptably low toxicity, for example, they have almost no CYP inhibitory activity and almost no hepatotoxicity, and thus can be safely used as an active pharmaceutical ingredient.

[Application to Pharmaceuticals]

The compounds of the present invention have a selective Btk inhibitory activity and as a result are useful as agents for preventing and/or treating Btk-related diseases, i.e., diseases in which B cells and/or mast cells participate, for example, allergic diseases, autoimmune diseases, inflammatory diseases, thromboembolic diseases, cancers, and graft-versus-host diseases. The compounds of the present invention also exercise a selective inhibitory action on B cell activation and as a result are also effective as inhibitors of B cell activation.

The allergic diseases in the present invention can be exemplified by allergies, anaphylaxis, allergic conjunctivitis, allergic rhinitis, and allergic dermatitis.

The autoimmune diseases in the present invention can be exemplified by inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Basedow's disease, Sjögren's syndrome, multiple sclerosis, Guillain-Barré syndrome, acute disseminated encephalomyelitis, Addison's disease, opsoclonus-myoclonus syndrome, ankylosing spondylitis, anti-phospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu's arteritis, temporal arteritis, warm autoimmune hemolytic anemia, Wegener's granuloma, psoriasis, alopecia universalis, Behçet's disease, chronic fatigue syndrome, dysautonomia, endometriosis, interstitial cystitis, myotonia, vulvodynia, and systemic lupus erythematosus.

The inflammatory diseases in the present invention can be exemplified by asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, epicondylitis, epididymitis, fasciitis, fibrositis, gastritis, gastroenteritis, hepatitis, hidradenitis suppurativa, laryngitis, mastitis, meningitis, myelitis, myocarditis, myositis, nephritis, oophoritis, orchitis, osteitis, pancreatitis, parotitis, pericarditis, peritonitis, pharyngitis, pleuritis, phlebitis, pneumonia, proctitis, prostatitis, pyelonephritis, rhinitis, salpingitis, sinusitis, stomatitis, synovitis, tendinitis, tonsillitis, uveitis, vaginitis, vasculitis, and vulvitis.

The thromboembolic diseases in the present invention can be exemplified by myocardial infarction, angina pectoris, reocclusion after angioplasty, restenosis after angioplasty, reocclusion after aortocoronary bypass, restenosis after aortocoronary bypass, stroke, transient ischemia, peripheral arterial occlusive disorders, pulmonary embolism, and deep venous thrombosis.

In the present invention, the cancers include non-Hodgkin's lymphomas, among which B-cell non-Hodgkin's lymphomas are particularly suitable, for example, Burkitt's lymphoma, AIDS-related lymphoma, marginal zone B-cell lymphoma (nodal marginal zone B-cell lymphoma, extranodal marginal zone B-cell lymphoma, and splenic marginal zone B-cell lymphoma), diffuse large B-cell lymphoma, primary effusion lymphoma, lymphomatoid granulomatosis, follicular lymphoma, B-cell chronic lymphocytic leukemia, B-cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma, and hairy cell leukemia. In addition to non-Hodgkin's lymphoma, the cancers in the present invention include pancreatic endocrine tumors, for example, insulinoma, gastrinoma, glucagonoma, somatostatinoma, VIPoma, PPoma, and GRFoma.

A compound of the present invention may be administered by itself or may be administered as a combined preparation combined with another drug for the purpose of
1) supplementing and/or enhancing the prophylactic and/or therapeutic effect of the compound,
2) improving the pharmacokinetics and absorption and reducing the dose of the compound, and/or
3) reducing the adverse reactions of the compound.

The combined preparation of a compound of the present invention with another drug may be administered in the form of a compounded agent in which both components are compounded in a single formulation or may be administered as separate formulations. Administration as separate formulations includes simultaneous administration and administration at different times. In the case of administration at different times, the compound of the present invention may be administered first followed by administration of the other drug, or the other drug may be administered first followed by the administration of the compound of the present invention. The same method of administration may be used for each or different methods of administration may be used.

There is no particular limitation on the diseases that may be subjected to the prevention and/or treatment by the aforementioned combined preparation, and this combined preparation may be used with any disease with which the prevention and/or treatment effect of the compound of the present invention is supplemented and/or enhanced.

This other drug for supplementing and/or enhancing the prophylactic and/or therapeutic effect of the compounds of the present invention against allergic diseases can be exemplified by antihistamines, leukotriene antagonists, antiallergic drugs, thromboxane A2 receptor antagonists, thromboxane synthase inhibitors, and steroids.

The other drug for supplementing and/or enhancing the prophylactic and/or therapeutic effect of the compounds of the present invention against autoimmune diseases can be exemplified by immunosuppressants; steroids; disease-modifying anti-rheumatic drugs; elastase inhibitors; cannabinoid-2 receptor agonists; prostaglandins; prostaglandin synthase inhibitors; phosphodiesterase inhibitors; metalloprotease inhibitors; adhesion molecule inhibitors; anti-cytokine protein agents such as anti-TNF-α agents, anti-IL-1 agents, and anti-IL-6 agents; cytokine inhibitors; nonsteroidal antiinflammatories; and anti-CD20 antibodies.

The other drug for supplementing and/or enhancing the prophylactic and/or therapeutic effect of the compounds of the present invention against inflammatory diseases can be exemplified by steroids, elastase inhibitors, cannabinoid-2 receptor agonists, prostaglandins, prostaglandin synthase inhibitors, phosphodiesterase inhibitors, metalloprotease inhibitors, adhesion molecule inhibitors, anti-leukotrienes, anti-cholinergic agents, thromboxane A2 receptor antagonists, thromboxane synthase inhibitors, xanthine derivatives, expectorants, antibacterials, antihistamines, anti-cytokine protein agents, cytokine inhibitors, forskolin agents, mediator release inhibitors, and nonsteroidal antiinflammatories.

The other drug for supplementing and/or enhancing the prophylactic and/or therapeutic effect of the compounds of the present invention against thromboembolic diseases can be exemplified by thrombolytic agents, heparin, heparinoids, low molecular weight heparins, warfarin, thrombin inhibitors, factor Xa inhibitors, ADP receptor antagonists, and cyclooxygenase inhibitors.

The other drug for supplementing and/or enhancing the prophylactic and/or therapeutic effect of the compounds of the present invention against non-Hodgkin's lymphomas can be exemplified by alkylating agents, antimetabolites, anticancer antibiotics, plant alkaloids, hormones, platinum compounds, anti-CD20 antibodies, and other anticancer agents.

The antihistamines can be exemplified by azelastine hydrochloride, ebastine, epinastine hydrochloride, emedastine fumarate, auranofin, oxatomide, olopatadine hydrochloride, dl-chlorpheniramine maleate, clemastine fumarate, ketotifen fumarate, cimetidine, dimenhydrinate, diphenhydramine hydrochloride, cyproheptadine hydrochloride, cetirizine hydrochloride, desloratadine, terfenadine, famotidine, fexofenadine hydrochloride, bepotastine, bepotastine besilate, mizolastine, mequitazine, mometasone furoate, ranitidine, ranitidine hydrochloride, loratadine, promethazine hydrochloride, and homochlorcyclizine hydrochloride.

The leukotriene antagonists can be exemplified by pranlukast hydrate, montelukast sodium, zafirlukast, ablukast, pobilukast, sulukast, iralukast sodium, verlukast, ritolukast, cinalukast, pirodomast, tomelukast, and doqualast.

The antiallergic drugs can be exemplified by amlexanox, azelastine hydrochloride, israpafant, ibudilast, imitrodast sodium, ebastine, epinastine hydrochloride, emedastine fumarate, oxatomide, ozagrel hydrochloride, olopatadine hydrochloride, cromoglicic acid, sodium cromoglicate, ketotifen fumarate, seratrodast, cetirizine hydrochloride, suplatast tosilate, tazanolast, terfenadine, domitroban calcium hydrate, tranilast, nedocromil, fexofenadine, fexofenadine hydrochloride, pemirolast potassium, mequitazine, ramatroban, repirinast, and loratadine.

The thromboxane A2 receptor antagonists can be exemplified by seratrodast, domitroban calcium hydrate, and ramatroban.

The thromboxane synthase inhibitors can be exemplified by imitrodast sodium and ozagrel hydrochloride.

The steroids can be exemplified by amcinonide, hydrocortisone sodium succinate, prednisolone sodium succinate, methylprednisolone sodium succinate, ciclesonide, difluprednate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasone furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethason acetate, halopredone acetate, fludrocortisone acetate, prednisolone acetate, methylprednisolone acetate, clobetasone butyrate, hydrocortisone butyrate, hydrocortisone butyrate propionate, and betamethasone butyrate propionate.

The immunosuppressants can be exemplified by azathioprine, ascomycin, everolimus, salazosulfapyridine, cyclosporine, cyclophosphamide, sirolimus, tacrolimus, bucillamine, methotrexate, and leflunomide.

The disease-modifying anti-rheumatic drugs can be exemplified by D-penicillamine, actarit, auranofin, salazosulfapyridine, hydroxychloroquine, bucillamine, methotrexate, leflunomide, lobenzarit sodium, aurothioglucose, and sodium aurothiomalate.

The elastase inhibitors can be exemplified by ONO—5046, ONO—6818, MR-889, PBI-1101, EPI-HNE-4, R-665, ZD-0892, ZD-8321, GW-311616, DMP-777, L-659286, L-680833, L-683845, and AE-3763.

The prostaglandins (abbreviated below as "PG") can be exemplified by PGE1 drugs (examples: alprostadil alfadex, alprostadil), PGI2 drugs (example: beraprost sodium), PG receptor agonists, and PG receptor antagonists. The PG receptor can be exemplified by PGE receptors (EP1, EP2, EP3, and EP4), PGD receptors (DP, CRTH2), PGF receptors (FP), PGI2 receptors (IP), and TX receptors (TP).

The prostaglandin synthase inhibitors can be exemplified by salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam cinnamate, zaltoprofen, and pranoprofen.

The phosphodiesterase inhibitors can be exemplified by rolipram, cilomilast, Bay19-8004, NIK-616, roflumilast (BY-217), cipamfylline (BRL-61063), atizoram (CP-80633), ONO—6126, SCH-351591, YM-976, V-11294A, PD-168787, D-4396, and IC-485.

The adhesion molecule inhibitors can be exemplified by α4 integrin antagonist.

The anti-TNF-α agents can be exemplified by anti-TNF-α antibodies, soluble TNF-α receptor, anti-TNF-α receptor antibodies, and soluble TNF-α binding protein and particularly by infliximab and etanercept.

The anti-IL-1 agents can be exemplified by anti-IL-1 antibodies, soluble IL-1 receptor, anti-IL-1Ra antibodies and/or anti-IL-1 receptor antibodies and particularly by anakinra.

The anti-IL-6 agents can be exemplified by anti-IL-6 antibodies, soluble IL-6 receptor, and anti-IL-6 receptor antibodies and particularly by tocilizumab.

The cytokine inhibitors can be exemplified by suplatast tosylate, T-614, SR-31747, and sonatimod.

The anti-cholinergic agents can be exemplified by trihexyphenidyl, trihexyphenidyl hydrochloride, biperiden, and biperiden hydrochloride.

The xanthine derivatives can be exemplified by aminophylline, theophylline, doxofylline, sipamphylline, and diprophylline.

The expectorants can be exemplified by foeniculated ammonia spirit, sodium bicarbonate, bromhexine hydrochloride, carbocysteine, ambroxol hydrochloride, methylcysteine hydrochloride, acetylcysteine, ethyl L-cysteine hydrochloride, and tyloxapol.

The antibacterials can be exemplified by sodium cefuroxime, meropenem trihydrate, netilmicin sulfate, sisomicin sulfate, ceftibuten, PA-1806, IB-367, tobramycin, PA-1420, doxorubicin, astromicin sulfate, and cefetamet pivoxil hydrochloride.

The mediator release inhibitors can be exemplified by tranilast, sodium cromoglicate, amlexanox, repirinast, ibudilast, dazanolast, and pemirolast potassium.

The thrombolytic agents can be exemplified by alteplase, urokinase, tisokinase, nasaruplase, nateplase, t-PA, pamiteplase, monteplase, prourokinase, and streptokinase.

The heparinoids can be exemplified by fondaparinux.

The low molecular weight heparins can be exemplified by danaparoid sodium, enoxaparin (sodium), nadroparin calcium, bemiparin (sodium), reviparin (sodium), and tinzaparin (sodium).

The thrombin inhibitor can be exemplified by argatroban, ximelagatran, melagatran, dabigatran, bivalirudin, lepirudin, hirudin, and desirudin.

The ADP receptor antagonists can be exemplified by ticlopidine hydrochloride and clopidogrel sulfate.

The cyclooxygenase inhibitors can be exemplified by aspirin.

The alkylating agents can be exemplified by nitrogen mustard N-oxide hydrochloride, cyclophosphamide, ifosfamide, melphalan, thiotepa, carboquone, busulfan, nimustine hydrochloride, dacarbazine, and ranimustine.

The antimetabolites can be exemplified by methotrexate, mercaptopurine, 6-mercaptopurine riboside, fluorouracil, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, and hydroxycarbamide.

The anticancer antibiotics can be exemplified by actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, and zinostatin stimalamer.

The plant alkaloids can be exemplified by vinblastine sulfate, vincristine sulfate, vindesine sulfate, irinotecan hydrochloride, etoposide, flutamide, vinorelbine tartrate, docetaxel hydrate, and paclitaxel.

The hormones can be exemplified by estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, and exemestane.

The platinum compounds can be exemplified by carboplatin, cisplatin, and nedaplatin.

The anti-CD-20 antibodies can be exemplified by rituximab, ibritumomab, and ocrelizumab.

The other anti-cancer agents can be exemplified by L-asparaginase, octreotide acetate, porfimer sodium, and mitoxantrone acetate.

The combined preparation comprising a combination with a compound of the present invention not only includes the combined preparations discovered to date, but also includes combined preparations that may be discovered in the future.

The compounds of the present invention are generally administered systemically or locally as a pharmaceutically effective component in an oral or parenteral form. The oral formulations can be exemplified by liquids for oral administration (for example, elixirs, syrups, pharmaceutically acceptable water-based formulations, suspensions, and emulsions) and solids for oral administration (for example, tablets (including sublingual tablets and orally disintegrating tablets), pills, capsules (including hard capsules, soft capsules, gelatin capsules, and microcapsules), powders, granules, and lozenges). The parenteral formulations can be exemplified by solutions (for example, injectables (for example, subcutaneous injectables, intravenous injectables, intramuscular injectables, intraperitoneal injectables, and drip formulations), eye drops (for example, aqueous eye drops (for example, aqueous eye drops, aqueous eye drop suspensions, viscous eye drops, and solubilized eye drops) and nonaqueous eye drops (for example, nonaqueous eye drops and nonaqueous eye drop suspensions)), topicals (for example, ointments (for example, ophthalmic ointments)), and ear drops. These formulations may be controlled release formulations such as rapid release formulations, sustained release formulations, and so forth. These formulations can be produced by known methods, for example, by the methods described in The Japanese Pharmacopoeia.

The liquids for oral administration within the sphere of oral formulations can be produced, for example, by dissolving, suspending, or emulsifying the effective component in a commonly used diluent (for example, purified water, ethanol, or a mixture thereof). These liquid formulations may also contain, for example, a wetting agent, suspending agent, emulsifying agent, sweetener, flavorant, fragrance, preservative, buffer, and so forth.

The solids for oral administration within the sphere of oral formulations can be prepared by mixing the effective component with, for example, a vehicle (for example, lactose, mannitol, glucose, microcrystalline cellulose, and starch), a binder (for example, hydroxypropyl cellulose, polyvinylpyrrolidone, and magnesium metasilicate aluminate), a disintegrant (for example, cellulose calcium glycolate), a lubricant (for example, magnesium stearate), a stabilizer, a dissolution adjuvant (for example, glutamic acid and aspartic acid), and so forth, and formulating according to standard methods. As necessary, coating may be carried out with a coating agent (for example, sugar, gelatin, hydroxypropyl cellulose, and hydroxypropyl methyl cellulose phthalate) and two or more layers may be applied.

Within the sphere of parenteral formulations, a topical may be produced using a known method or a formulation in common use. For example, an ointment may be prepared by incorporating or melting the effective component into a base. The ointment base is selected from known ointment bases or an ointment base in common use. For example, a single selection from the following or a mixture of two or more selections from the following may be used: higher fatty acids and higher fatty acid esters (for example, adipic acid, myristic acid, palmitic acid, stearic acid, oleic acid, adipate esters, myristate esters, palmitate esters, stearate esters, and oleate esters), waxes (for example, beeswax, spermaceti, and ceresin), surfactants (for example, polyoxyethylene alkyl ether phosphate esters), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg yolk oil, squalane, and squalene), water, absorption promoters, and anti-irritants. A humectant, preservative, stabilizer, antioxidant, fragrance, and so forth may also be incorporated.

Injectables within the sphere of parenteral formulations encompass solutions, suspensions, and emulsions as well as solid injectables used by dissolution or suspension in a solvent at the time of use. For example, an injectable may be used in which the effective component is dissolved, suspended, or emulsified in a solvent. For example, distilled water for injection, physiological saline solution, a plant oil, propylene glycol, polyethylene glycol, an alcohol such as ethanol, or a combination of the preceding may be used for the solvent. The injectable may also contain a stabilizer, a dissolution adjuvant (for example, glutamic acid, aspartic acid, and Polysorbate 80 (registered trade mark)), a suspending agent, an emulsifying agent, a soothing agent, a buffer, a preservative, and so forth.

The injectable may be sterilized in the final step or may be manufactured using aseptic processing. The injectable may also be manufactured as a sterile solid form, for example, a freeze-dried product, and may be used after dissolution in distilled water for injection or another solvent, which is either sterile or sterilized prior to use.

The dose when a compound of the present invention is used as an effective component in a drug may be selected as appropriate depending upon, for example, the symptoms, age, type of formulation, and so forth. In the case of an oral formulation, preferably from 1 mg to 100 mg and more preferably from 5 mg to 30 mg may be administered from one to several times per day (for example, one to three times). In the case of eye drops, from one to several drops per administration of an ophthalmic solution having a concentration of preferably 0.000001% to 5% (w/v) and more preferably 0.00001% to 0.05% (w/v) may be instilled from one to several times per day (for example, from one to eight times). In the case of an ophthalmic ointment, an ophthalmic ointment with a concentration of preferably 0.000001% to 5% (w/w) and more preferably 0.00001% to 0.05% (w/w) may be applied from one to several times per day (for example, one to four times).

Of course, as noted above, the dose will depend upon various conditions and as a result cases will occur in which an amount less than the aforementioned dosage levels will be sufficient or in which these ranges must be exceeded.

EXAMPLES

The present invention is described below using examples, but the present invention is not limited by these examples.

The solvents given in parentheses for TLC and in the sections on chromatographic separation indicate the elution solvents or development solvents used, and the proportions are volume ratios.

Unless specifically indicated otherwise, the NMR data is data for $^1$H-NMR.

The solvent used in the measurement is given in parentheses in the NMR section.

The compound names used in this Description are generally names generated based on IUPAC naming rules or generated using ACD/Name (registered trademark), a computer program from Advanced Chemistry Development, Inc., that performs naming based on IUPAC rules.

Example 1

N,N-dibenzyl-6-chloro-5-nitropyrimidine-4-amine

Dibenzylamine (10.2 g) in a dichloromethane (30 mL) solution was added dropwise on an ice bath to a dichloromethane (70 mL) solution of 4,6-dichloro-5-nitropyrimidine (10 g). This was followed by the addition of triethylamine (14.4 mL) and stirring for 1 hour. Water was then added to the reaction mixture and the organic layer was subsequently washed with saturated aqueous sodium chloride solution and dried over anhydrous sodium sulfate. The solvent was concentrated under reduced pressure to obtain the title compound (19.2 g) having the physical property value indicated below. TLC: Rf 0.50 (hexane:ethyl acetate=7:1).

Example 2 tert-butyl 3-{[6-(dibenzylamino)-5-nitropyrimidin-4-yl]amino}azetidine-1-carboxylate The compound (10.3 g) prepared in Example 1 and tert-butyl 3-aminoazetidine-1-carboxylate (5.0 g) were dissolved in dioxane (58 mL); triethylamine (8.1 mL) was added; and stirring was then carried out for 5 hours at 50° C. The reaction mixture was returned to room temperature; the solvent was then distilled off; water was added; and extraction was performed with ethyl acetate. The organic layer was washed with saturated aqueous sodium chloride solution and subsequently dried over anhydrous sodium sulfate and the solvent was then distilled off. The residue was purified by silica gel column chromatography to obtain the title compound (10.8 g) having the physical property value indicated below. TLC: Rf 0.40 (hexane:ethyl acetate=4:1).

Example 3 tert-butyl 3-{[5-amino-6-(dibenzylamino)pyrimidin-4-yl]amino}azetidine-1-carboxylate An ethyl acetate (360 mL) solution of the compound (17.5 g) prepared in Example 2 was added dropwise to a mixture of zinc (23.3 g) and a 3.0 M aqueous ammonium chloride solution (11.4 g) on an ice bath and the temperature was immediately raised to room temperature. After stirring for 2 hours, the reaction mixture was filtered on Celite (trade name) and the solvent was then distilled off. The residue was purified by silica gel column chromatography to obtain the title compound (12.4 g) having the physical property value indicated below. TLC: Rf 0.69 (hexane:ethyl acetate=1:1).

Example 4 tert-butyl 3-[6-(dibenzylamino)-8-oxo-7,8-dihydro-9H-purin-9-yl]azetidine-1-carboxylate The compound (8.4 g) prepared in Example 3 and 1,1'-carbonyldiimidazole (5.9 g) were dissolved in tetrahydrofuran (120 mL) followed by stirring for 15 hours at 60° C. After the solvent had been distilled from the reaction mixture, water was added and extraction with ethyl acetate was performed. The organic layer was washed with saturated aqueous sodium chloride solution and dried over anhydrous sodium sulfate and the solvent was then distilled off. The residue was purified by silica gel column chromatography to obtain the title compound (7.8 g) having the physical property value indicated below.
TLC: Rf 0.28 (hexane:ethyl acetate=2:1).

Example 5 tert-butyl 3-(6-amino-8-oxo-7,8-dihydro-9H-purin-9-yl)azetidine-1-carboxylate

The compound (7.8 g) prepared in Example 4 was dissolved in methanol (240 mL) and ethyl acetate (50 mL); 20% Pearlman's catalyst (Pd(OH)$_2$/C) (8.0 g, 100 wt %) was added; replacement with hydrogen was carried out; and stirring was performed for 7.5 hours at 60° C. The reaction mixture was filtered on Celite (trade name) and the solvent was distilled off to obtain the title compound (5.0 g) having the physical property value indicated below.
TLC: Rf 0.50 (ethyl acetate).

Example 6 tert-butyl 3-[6-amino-8-oxo-7-(4-phenoxyphenyl)-7,8-dihydro-9H-purin-9-yl]azetidine-1-carboxylate p-phenoxyphenylboric acid (2.1 g), copper(II) acetate (1.48 g), molecular sieve 4 A (2.5 g), and pyridine (0.82 mL) were added at room temperature to a dichloromethane (200 mL) suspension of the compound (2.5 g) prepared in Example 5, followed by stirring for 21 hours. The reaction solution was filtered on Celite (trade name) and the residue was purified by silica gel column chromatography to obtain the title compound (1.3 g) having the physical property value indicated below. TLC: Rf 0.18 (hexane:ethyl acetate=1:1).

Example 7

6-amino-9-azetidin-3-yl-7-(4-phenoxyphenyl)-7,9-dihydro-8H-purin-8-one dihydrochloride 4 N hydrochloric acid/dioxane (13 mL) was added at room temperature to a suspension in methanol (13 mL) of the compound (1.3 g, 2.76 mmol, 1.0 equivalent) prepared in Example 6 and stirring was carried out for 1 hour. The solvent was then distilled off to obtain the title compound (1.5 g) having the physical property value indicated below.

TLC: Rf 0.50 (dichloromethane:methanol:28% aqueous ammonia=9:1:0.1).

Example 8

9-(1-acryloyl-3-azetidinyl)-6-amino-7-(4-phenoxyphenyl)-7,9-dihydro-8H-purin-8-one

[C 23]

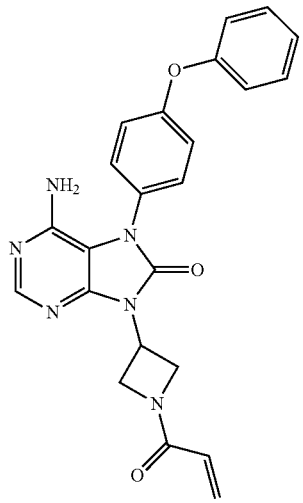

Triethylamine (1.1 mL) was added to a suspension in dichloromethane (16 mL) of the compound (1.5 g) prepared in Example 7 and a dichloromethane (10 mL) solution of acryloyl chloride (0.32 mL) was then added dropwise at −10° C. The solvent was distilled from the reaction mixture followed by the addition of water and extraction with methylene chloride. The organic layer was washed with a saturated aqueous sodium chloride solution and dried over anhydrous sodium sulfate and the solvent was distilled off. The residue was purified by silica gel column chromatography to obtain the title compound (0.8 g) having the physical property values indicated below.

TLC: Rf 0.43 (ethyl acetate);
$^1$H-NMR (CDCl$_3$): δ 4.47-4.61, 4.83-4.88, 5.06-5.11, 5.37-5.47, 5.70-5.74, 6.21-6.30, 6.36-6.43, 7.07-7.23, 7.35-7.44, 8.24.

Example 8(1) to Example 8(22)

The exemplary compounds given below were obtained by following the same process template as in Example 1→Example 2→Example 3→Example 4→Example 5→Example 6→Example 7→Example 8, using 4,6-dichloro-5-nitropyrimidine, using tert-butyl 3-aminoazetidine-1-carboxylate or the corresponding amine derivative in its place, using acryloyl chloride or the corresponding acid chloride in its place, and using p-phenoxyphenylboric acid or the corresponding boric acid in its place.

Example 8(1)

9-[(3R)-1-acryloyl-3-piperidinyl]-6-amino-7-(4-phenoxyphenyl)-7,9-dihydro-8H-purin-8-one TLC: Rf 0.33 (ethyl acetate);
$^1$H-NMR (CDCl$_3$): δ 1.64-1.78, 1.90-2.12, 2.55-2.80, 3.10-3.22, 3.63-3.74, 3.99-4.12, 4.40-4.55, 4.73-4.82, 5.66-5.72, 6.26-6.31, 6.53-6.65, 7.07-7.22, 7.36-7.44, 8.23.

Example 8(2)

9-(1-acryloyl-3-azetidinyl)-6-amino-7-[4-(3-chlorophenoxy)-3-methoxyphenyl]-7,9-dihydro-8H-purin-8-one TLC: Rf 0.25 (ethyl acetate);
$^1$H-NMR (CDCl$_3$): δ 3.88, 4.47-4.62, 4.83-4.89, 5.07-5.12, 5.39-5.48, 5.70-5.74, 6.21-6.30, 6.37-6.43, 6.87-6.91, 6.95-7.00, 7.08-7.13, 7.24-7.29, 8.27.

Example 8(3)

9-(1-acryloyl-4-piperidinyl)-6-amino-7-(4-phenoxyphenyl)-7,9-dihydro-8H-purin-8-one TLC: Rf 0.38 (ethyl acetate);
$^1$H-NMR (CDCl$_3$): δ 1.88-1.96, 2.59-2.80, 3.15-3.27, 4.13-4.22, 4.48, 4.58-4.69, 4.85-4.95, 5.69-5.73, 6.27-6.34, 6.59-6.68, 7.07-7.15, 7.17-7.22, 7.34-7.44, 8.21.

Example 8(4)

9-[(3R)-1-acryloyl-3-pyrrolidinyl]-6-amino-7-(4-phenoxyphenyl)-7,9-dihydro-8H-purin-8-one TLC: Rf 0.60 (chloroform:methanol:aqueous ammonia=80:10:1);
$^1$H-NMR (CDCl$_3$): δ 2.21-2.46, 2.82-3.08, 3.53-3.76, 3.89-4.36, 4.40-4.59, 5.11-5.32, 5.64-5.77, 6.34-6.58, 7.04-7.24, 7.34-7.49, 8.18-8.26.

Example 8(5)

9-[(3S)-1-acryloyl-3-piperidinyl]-6-amino-7-(4-phenoxyphenyl)-7,9-dihydro-8H-purin-8-one TLC: Rf 0.71 (chloroform:methanol:aqueous ammonia=80:10:1);
$^1$H-NMR (CDCl$_3$): δ 1.52-1.80, 1.88-2.17, 2.51-2.84, 3.07-3.26, 3.59-3.76, 3.94-4.16, 4.38-4.63, 4.66-4.90, 5.61-5.80, 6.21-6.40, 6.48-6.72, 7.03-7.25, 7.33-7.50, 8.23.

Example 8(6)

9-[(3S)-1-acryloyl-3-pyrrolidinyl]-6-amino-7-(4-phenoxyphenyl)-7,9-dihydro-8H-purin-8-one TLC: Rf 0.50 (ethyl acetate:methanol=19:1);
$^1$H-NMR (CDCl$_3$): δ 2.23-2.43, 2.84-3.04, 3.55-3.73, 3.91-4.08, 4.12-4.19, 4.26-4.32, 4.47-4.49, 5.13-5.27, 5.66-5.73, 6.35-6.54, 7.03-7.28, 7.33-7.43, 8.20-8.22.

Example 8(7)

9-(1-acryloyl-3-azetidinyl)-6-amino-7-[4-(3-chlorophenoxy)phenyl]-7,9-dihydro-8H-purin-8-one TLC: Rf 0.53 (chloroform:methanol:aqueous ammonia=9:1:0.01);
$^1$H-NMR (CDCl$_3$): δ 4.46-4.61, 4.85, 5.08, 5.42, 5.71, 6.24, 6.38, 6.96, 7.08, 7.13-7.18, 7.32, 7.42, 8.24.

Example 8(8)

9-(1-acryloyl-3-azetidinyl)-6-amino-7-(3-methoxy-4-phenoxyphenyl)-7,9-dihydro-8H-purin-8-one TLC: Rf 0.18 (ethyl acetate);
$^1$H-NMR (CDCl$_3$): δ 3.90, 4.45-4.65, 4.80-4.90, 5.05-5.15, 5.35-5.45, 5.72, 6.26, 6.39, 6.90-7.40, 8.25.

Example 8(9)

9-(1-acryloyl-3-azetidinyl)-6-amino-7-(3-fluoro-4-phenoxyphenyl)-7,9-dihydro-8H-purin-8-one TLC: Rf 0.27 (ethyl acetate);
$^1$H-NMR (CDCl$_3$): δ 4.45-4.65, 4.80-4.90, 5.05-5.15, 5.35-5.45, 5.72, 6.25, 6.40, 7.05-7.42, 8.26.

Example 8(10)

9-(1-acryloyl-3-azetidinyl)-6-amino-7-[4-(3,4-dichlorophenoxy)-3-methoxyphenyl]-7,9-dihydro-8H-purin-8-one TLC: Rf 0.20 (ethyl acetate);
$^1$H-NMR (CD$_3$OD): δ 3.82, 4.47, 4.59, 4.72, 4.77-4.95, 5.00-5.09, 5.40-5.53, 5.77, 6.28, 6.41, 6.91, 7.09, 7.28, 7.43, 8.17.

Example 8(11)

9-(1-acryloyl-3-azetidinyl)-6-amino-7-[4-(3-fluorophenoxy)phenyl]-7,9-dihydro-8H-purin-8-one TLC: Rf 0.73 (ethyl acetate:methanol:triethylamine=9:1:0.1);
$^1$H-NMR (CDCl$_3$): δ 4.50, 4.59, 4.85, 5.08, 5.42, 5.72, 6.25, 6.40, 6.78-6.93, 7.17, 7.33, 7.43, 8.26.

Example 8(12)

9-(1-acryloyl-3-azetidinyl)-6-amino-7-[4-(3,5-difluorophenoxy)phenyl]-7,9-dihydro-8H-purin-8-one TLC: Rf 0.78 (ethyl acetate:methanol:triethylamine=9:1:0.1);

$^1$H-NMR (CDCl$_3$): δ 4.50, 4.59, 4.85, 5.08, 5.42, 5.71, 6.25, 6.39, 6.57-6.62, 7.19, 7.45, 8.26.

Example 8(13)

9-(1-acryloyl-3-azetidinyl)-6-amino-7-(2-fluoro-4-phenoxyphenyl)-7,9-dihydro-8H-purin-8-one TLC: Rf 0.47 (methanol:ethyl acetate=1:19);
$^1$H-NMR (CDCl$_3$): δ 4.40-4.60, 4.80-4.90, 5.00-5.10, 5.35-5.45, 5.72, 6.25, 6.39, 6.80-7.50, 8.24.

Example 8(14)

9-[(1-acryloyl-4-piperidinyl)methyl]-6-amino-7-(4-phenoxyphenyl)-7,9-dihydro-8H-purin-8-one

[C 24]

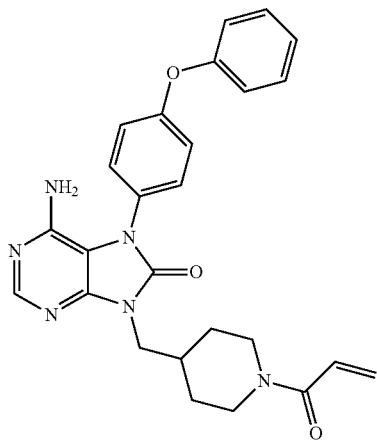

TLC: Rf 0.50 (ethyl acetate:methanol=19:1);
$^1$H-NMR (CDCl$_3$): δ 1.27-1.44, 1.72-1.86, 2.18-2.37, 2.66, 3.04, 3.90, 4.00, 4.51, 4.67, 5.66, 6.24, 6.56, 7.03-7.24, 7.32-7.46, 8.25.

Example 8(15)

6-amino-9-[1-(chloroacetyl)-3-azetidinyl]-7-(4-phenoxyphenyl)-7,9-dihydro-8H-purin-8-one TLC: Rf 0.41 (ethyl acetate:methanol=19:1);
$^1$H-NMR (CDCl$_3$): δ 3.96-4.05, 4.44-4.53, 4.62-4.72, 4.80-4.87, 5.08-5.16, 5.38-5.48, 7.05-7.24, 7.35-7.43, 8.24.

Example 8(16)

6-amino-9-[(3R)-1-(chloroacetyl)-3-pyrrolidinyl]-7-(4-phenoxyphenyl)-7,9-dihydro-8H-purin-8-one TLC: Rf 0.49 (ethyl acetate:methanol=19:1);
$^1$H-NMR (CDCl$_3$): δ 2.20-2.48, 2.78-3.01, 3.50-3.63, 3.64-3.81, 3.90-4.19, 4.26-4.36, 4.51, 5.14-5.32, 7.02-7.26, 7.27-7.46, 8.21.

Example 8(17)

6-amino-9-{(3R)-1-[(2E)-2-butenoyl]-3-pyrrolidinyl}-7-(4-phenoxyphenyl)-7,9-dihydro-8H-purin-8-one TLC: Rf 0.41 (ethyl acetate:methanol=19:1);
$^1$H-NMR (CDCl$_3$): δ 1.88, 2.19-2.43, 2.82-3.05, 3.50-3.74, 3.88-4.18, 4.20-4.30, 4.48, 5.08-5.16, 6.13, 6.95, 7.05-7.23, 7.34-7.46, 8.22.

Example 8(18)

6-amino-9-{[1-(chloroacetyl)-4-piperidinyl]methyl}-7-(4-phenoxyphenyl)-7,9-dihydro-8H-purin-8-one TLC: Rf 0.54 (ethyl acetate:methanol=19:1);
$^1$H-NMR (CDCl$_3$): δ 1.14-1.59, 1.70-1.87, 2.19-2.37, 2.65, 3.10, 3.81-3.95, 3.91, 4.06, 4.50, 4.51-4.63, 7.05-7.23, 7.34-7.46, 8.25.

Example 8(19)

9-[(1-acryloyl-4-methyl-4-piperidinyl)methyl]-6-amino-7-(4-phenoxyphenyl)-7,9-dihydro-8H-purin-8-one TLC: Rf 0.55 (ethyl acetate:methanol=9:1);
$^1$H-NMR (CDCl$_3$): δ1.15, 1.37-1.85, 3.21-3.50, 3.70-3.99, 4.03-4.23, 4.52-4.73, 5.64, 6.24, 6.56, 6.97-7.23, 7.31-7.50, 8.21.

Example 8(20)

6-amino-9-{1-[(2E)-2-butenoyl]-3-azetidinyl}-7-(4-phenoxyphenyl)-7,9-dihydro-8H-purin-8-one TLC: Rf 0.63 (ethyl acetate:methanol=9:1);
$^1$H-NMR (CDCl$_3$): δ 1.89, 4.46, 4.51, 4.79, 5.03, 5.20, 5.39, 5.94, 6.93, 7.07-7.10, 7.19, 7.36-7.43, 8.23.

Example 8(21)

9-{[(3R)-1-acryloyl-3-pyrrolidinyl]methyl}-6-amino-7-(4-phenoxyphenyl)-7,9-dihydro-8H-8-one TLC: Rf 0.49 (dichloromethane:methanol:aqueous ammonia=9:1:0.1);
$^1$H-NMR (CDCl$_3$): δ 1.77-1.97, 2.02-2.19, 2.83-3.01, 3.38-3.62, 3.66-3.83, 3.98-4.11, 4.42-4.54, 5.61-5.70, 6.30-6.45, 7.04-7.23, 7.36-7.43, 8.23.

Example 8(22)

9-{[(2S)-1-acryloyl-2-pyrrolidinyl]methyl}-6-amino-7-(4-phenoxyphenyl)-7,9-dihydro-8H-purin-8-one TLC: Rf 0.44 (dichloromethane:methanol:aqueous ammonia=9:1:0.1);
$^1$H-NMR (CDCl$_3$): δ 1.87-2.28, 3.46-3.78, 3.86-3.96, 3.99-4.10, 4.15-4.23, 4.40, 4.45-4.60, 4.81-4.91, 5.54-5.72, 6.16-6.44, 6.86-6.97, 7.04-7.22, 7.36-7.45, 8.21-8.26.

Example 9 tert-butyl (3R)-3-{[6-(dibenzylamino)-5-nitropyrimidin-4-yl]amino}piperidine-1-carboxylate The title compound (1.44 g) having the physical property value given below was obtained by following the same process template as in Example 2 using the compound (1.5 g) produced in Example 1 and using tert-butyl (3R)-3- aminopiperidine-1-carboxylate (0.85 g) in place of the tert-butyl 3-aminoazetidine-1-carboxylate.

TLC: Rf 0.23 (hexan:ethyl acetate=9:1).

Example 10

6-amino-7-(4-phenoxyphenyl)-9-[(3R)-piperidin-3-yl]-7,9-dihydro-8H-purin-8-one dihydrochloride The title compound (155 mg) having the physical property value given below was obtained by following the same process template as in Example 3→Example 4→Example 5→Example 6→Example 7, using the compound produced in Example 9 and using p-phenoxyphenylboric acid (154 mg).

TLC: Rf 0.68 (methanol:dichloromethane:aqueous ammonia=80:20:4).

Example 11

6-amino-9-{(3R)-1-[(2E)-4-(dimethylamino)-2-butenoyl]-3-piperidinyl}-7-(4-phenoxyphenyl)-7,9-dihydro-8H-purin-8-one

[C 25]

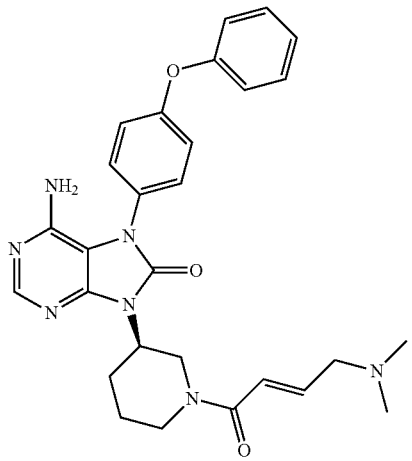

Triethylamine (1.40 mL) was added to a dichloromethane (6 mL) solution of the compound (1.20 g) produced in Example 10. 4-bromocrotonyl chloride (0.5 M dichloroethane solution, 5.04 mL) was added on an ice bath and the reaction mixture was stirred for 30 minutes on an ice bath. After concentration, a saturated aqueous sodium bicarbonate solution was added and ethyl acetate extraction was performed. The obtained organic layer was washed with a saturated aqueous sodium chloride solution and was dried over sodium sulfate, filtered, and concentrated. Tetrahydrofuran (6 mL) and dimethylamine (2.0 M tetrahydrofuran solution, 6.3 mL) were added to the residue and heating was carried out for 2 hours at 50° C. This was followed by filtration and then concentration. The resulting residue was purified by silica gel column chromatography (hexan:ethyl acetate=1:1→ethyl acetate→ethyl acetate:methanol:triethylamine=18:2:1) to yield the title compound (0.66 g) having the physical property values indicated below.

TLC: Rf 0.40 (ethyl acetate:methanol:triethylamine=18:2:1);

$^1$H-NMR (CDCl$_3$): δ 1.52-1.77, 1.87-2.00, 2.00-2.12, 2.18-2.35, 2.53-2.85, 2.93-3.22, 3.57-3.74, 3.97-4.17, 4.36-4.60, 4.66-4.89, 6.35-6.55, 6.76-6.94, 7.03-7.30, 7.32-7.48, 8.21.

Examples 11(1) to 11(26)

The exemplary compounds given below were obtained by following the same process template as in Example 9→Example 10→Example 11, using the compound produced in Example 1, using tert-butyl (3R)-3-aminopiperidine-1-carboxylate or the corresponding amine derivative in its place, using p-phenoxyphenylboric acid or the corresponding boric acid in its place, and using dimethylamine or the corresponding amine derivative in its place.

Example 11(1)

6-amino-9-{1-[(2E)-4-(dimethylamino)-2-butenoyl]-3-azetidinyl}-7-(4-phenoxyphenyl)-7,9-dihydro-8H-purin-8-one TLC: Rf 0.21 (ethyl acetate:methanol:triethylamine=9:1:0.5);

$^1$H-NMR (CDCl$_3$): δ 2.27, 3.08-3.10, 4.45-4.60, 4.80-4.86, 5.05-5.10, 5.36-5.44, 6.06-6.12, 6.87-6.96, 7.07-7.15, 7.17-7.23, 7.35-7.44, 8.24.

Example 11(2)

6-amino-9-{1-[(2E)-4-(4-morpholinyl)-2-butenoyl]-3-azetidinyl}-7-(4-phenoxyphenyl)-7,9-dihydro-8H-purin-8-one TLC: Rf 0.48 (ethyl acetate:methanol:triethylamine=9:1:0.5);

$^1$H-NMR (CDCl$_3$): δ 2.48, 3.14-3.16, 3.71-3.73, 4.44-4.59, 4.80-4.86, 5.04-5.09, 5.36-5.46, 6.08-6.13, 6.86-6.95, 7.07-7.15, 7.17-7.22, 7.34-7.42, 8.23.

Example 11(3)

6-amino-9-{(3R)-1-[(2E)-4-(dimethylamino)-2-butenoyl]-3-pyrrolidinyl}-7-(4-phenoxyphenyl)-7,9-dihydro-8H-purin-8-one

[C 26]

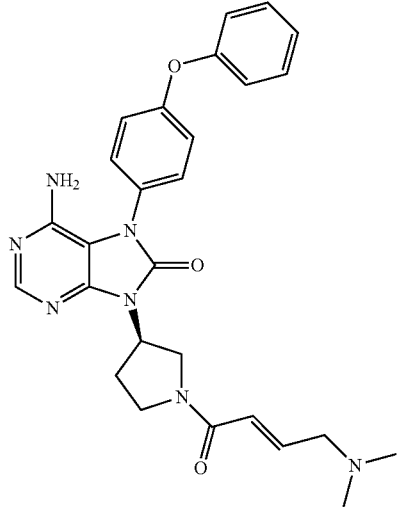

TLC: Rf 0.21 (dichloromethane:methanol=17:3);

$^1$H-NMR (CDCl$_3$): δ 2.20-2.42, 2.84-3.14, 3.52-3.76, 3.90-4.20, 4.22-4.34, 4.42-4.51, 5.10-5.29, 6.20-6.38, 6.86-7.01, 7.03-7.24, 7.37-7.46, 8.20-8.23.

Example 11(4)

6-amino-7-(4-phenoxyphenyl)-9-{1-[(2E)-4-(1-piperidinyl)-2-butenoyl]-3-azetidinyl}-7,9-dihydro-8H-purin-8-one TLC: Rf 0.48 (ethyl acetate:methanol:triethylamine=9:1:0.5);

$^1$H-NMR (CDCl$_3$): δ 1.32-1.47, 1.57-1.64, 2.38-2.44, 3.13-3.14, 4.44-4.60, 4.80-4.86, 5.04-5.09, 5.35-5.46, 6.05-6.11, 6.89-6.99, 7.07-7.15, 7.17-7.23, 7.35-7.44, 8.24.

Example 11(5)

6-amino-7-(4-phenoxyphenyl)-9-{1-[(2E)-4-(4-thiomorpholinyl)-2-butenoyl]-3-azetidinyl}-7,9-dihydro-8H-purin-8-one TLC: Rf 0.58 (ethyl acetate:methanol:triethylamine=9:1:0.5);

$^1$H-NMR (CDCl$_3$): δ 2.66-2.75, 3.15-3.17, 4.44-4.59, 4.80-4.86, 5.04-5.09, 5.36-5.44, 6.05-6.11, 6.85-6.94, 7.07-7.15, 7.17-7.23, 7.35-7.44, 8.24.

Example 11(6)

6-amino-9-{1-[(2E)-4-(3-oxo-1-piperazinyl)-2-butenoyl]-3-azetidinyl}-7-(4-phenoxyphenyl)-7,9-dihydro-8H-purin-8-one TLC: Rf 0.16 (ethyl acetate:methanol:triethylamine=9:1:0.5);

$^1$H-NMR (CDCl$_3$): δ 2.67-2.71, 3.19, 3.22-3.24, 3.36-3.40, 4.45-4.59, 4.81-4.87, 5.05-5.10, 5.37-5.47, 6.05, 6.10-6.16, 6.84-6.93, 7.07-7.15, 7.17-7.23, 7.36-7.44, 8.24.

Example 11(7)

6-amino-7-(4-phenoxyphenyl)-9-{1-[(2E)-4-(1-pyrrolidinyl)-2-butenoyl]-3-azetidinyl}-7,9-dihydro-8H-purin-8-one TLC: Rf 0.39 (ethyl acetate:methanol:triethylamine=9:1:0.5);

$^1$H-NMR (CDCl$_3$): δ 1.79-1.83, 2.50-2.65, 3.28-3.31, 4.44-4.60, 4.80-4.85, 5.04-5.09, 5.35-5.45, 6.10-6.15, 6.90-6.99, 7.06-7.14, 7.16-7.22, 7.35-7.43, 8.23.

Example 11(8)

6-amino-9-(1-{(2E)-4-[(2-hydroxyethyl)(methyl)amino]-2-butenoyl}-3-azetidinyl)-7-(4-phenoxyphenyl)-7,9-dihydro-8H-purin-8-one TLC: Rf 0.40 (dichloromethane:methanol:aqueous ammonia=9:1:0.1);

$^1$H-NMR (CDCl$_3$): δ 2.29, 2.57-2.61, 3.23-3.26, 3.59-3.63, 4.44-4.59, 4.80-4.86, 5.04-5.09, 5.36-5.46, 6.06-6.13, 6.86-6.95, 7.07-7.15, 7.16-7.26, 7.35-7.42, 8.24.

Example 11(9)

6-amino-7-(4-phenoxyphenyl)-9-{(3R)-1-[(2E)-4-(1-pyrrolidinyl)-2-butenoyl]-3-pyrrolidinyl}-7,9-dihydro-8H-purin-8-one TLC: Rf 0.42 (chloroform:methanol=9:1);

$^1$H-NMR (CDCl$_3$): δ 1.74-1.92, 2.15-2.43, 2.54-2.70, 2.82-3.06, 3.32, 3.49-3.77, 3.91-4.20, 4.23-4.36, 4.51, 5.10-5.28, 6.36, 6.91-7.04, 7.06-7.24, 7.37-7.45, 8.21.

Example 11(10)

6-amino-7-(4-phenoxyphenyl)-9-{(3R)-1-[(2E)-4-(1-piperidinyl)-2-butenoyl]-3-pyrrolidinyl}-7,9-dihydro-8H-purin-8-one TLC: Rf 0.39 (chloroform:methanol=9:1);

$^1$H-NMR (CDCl$_3$): δ 1.35-1.50, 1.51-1.65, 2.20-2.48, 2.82-3.06, 3.12, 3.52-3.75, 3.88-4.19, 4.21-4.33, 4.51, 5.09-5.28, 6.27, 6.88-7.04, 7.05-7.23, 7.34-7.44, 8.22.

Example 11(11)

6-amino-9-{(3R)-1-[(2E)-4-(4-morpholinyl)-2-butenoyl]-3-pyrrolidinyl}-7-(4-phenoxyphenyl)-7,9-dihydro-8H-purin-8-one TLC: Rf 0.51 (chloroform:methanol=9:1);

$^1$H-NMR (CDCl$_3$): δ 2.19-2.54, 2.83-3.05, 3.14, 3.51-3.77, 3.89-4.19, 4.21-4.32, 4.57, 5.10-5.28, 6.31, 6.87-6.99, 7.04-7.23, 7.34-7.46, 8.21.

Example 11(12)

6-amino-7-(4-phenoxyphenyl)-9-{(3R)-1-[(2E)-4-(4-thiomorpholinyl)-2-butenoyl]-3-pyrrolidinyl}-7,9-dihydro-8H-purin-8-one TLC: Rf 0.54 (chloroform:methanol=9:1);

$^1$H-NMR (CDCl$_3$): δ 2.10-2.43, 2.50-2.78, 2.82-3.06, 3.15, 3.51-3.74, 3.89-4.19, 4.22-4.33, 4.51, 5.09-5.28, 6.29, 6.86-6.99, 7.04-7.23, 7.35-7.47, 8.22.

Example 11(13)

6-amino-9-[(3R)-1-{(2E)-4-[ethyl(methyl)amino]-2-butenoyl}-3-pyrrolidinyl]-7-(4-phenoxyphenyl)-7,9-dihydro-8H-purin-8-one TLC: Rf 0.34 (ethyl acetate:methanol:triethylamine=9:1:0.5);

$^1$H-NMR (CDCl$_3$): δ 1.05-1.19, 2.20-2.43, 2.35, 2.59, 2.82-3.08, 3.31, 3.50-3.77, 3.90-4.20, 4.23-4.33, 4.50, 5.10-5.28, 6.38, 6.88-6.99, 7.04-7.23, 7.35-7.46, 8.21.

Example 11(14)

6-amino-9-{(3S)-1-[(2E)-4-(dimethylamino)-2-butenoyl]-3-pyrrolidinyl}-7-(4-phenoxyphenyl)-7,9-dihydro-8H-purin-8-one

[C 27]

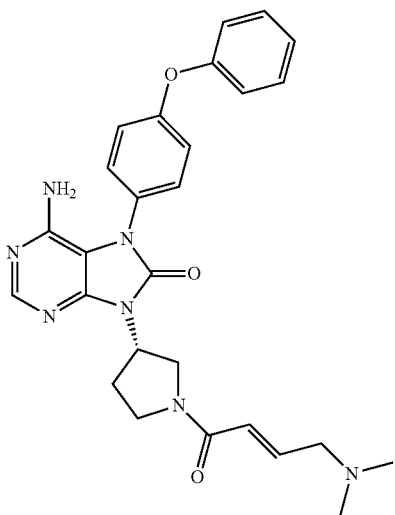

TLC: Rf 0.38 (dichloromethane:methanol:aqueous ammonia=9:1:0.1);
$^1$H-NMR (CDCl$_3$): δ 2.20-2.42, 2.83-3.14, 3.52-3.74, 3.92-4.20, 4.24-4.32, 4.42-4.51, 5.13-5.25, 6.20-6.38, 6.87-7.00, 7.05-7.24, 7.35-7.43, 8.20-8.23.

Example 11(15)

6-amino-9-{1-[(2E)-4-(diethylamino)-2-butenoyl]-3-azetidinyl}-7-(4-phenoxyphenyl)-7,9-dihydro-8H-purin-8-one TLC: Rf 0.47 (ethyl acetate:methanol:triethylamine=9:1:0.5);
$^1$H-NMR (CDCl$_3$): δ 1.01-1.06, 2.51-2.58, 3.25-3.27, 4.44-4.59, 4.81-4.86, 5.04-5.09, 5.36-5.46, 6.07-6.13, 6.91-7.00, 7.07-7.15, 7.17-7.23, 7.36-7.44, 8.24.

Example 11(16)

6-amino-9-(1-{(2E)-4-[ethyl(methyl)amino]-2-butenoyl}-3-azetidinyl)-7-(4-phenoxyphenyl)-7,9-dihydro-8H-purin-8-one TLC: Rf 0.50 (ethyl acetate:methanol:triethylamine=9:1:0.5);
$^1$H-NMR (CDCl$_3$): δ 1.05-1.09, 2.24, 2.41-2.48, 3.15-3.18, 4.44-4.59, 4.80-4.86, 5.04-5.09, 5.36-5.46, 6.05-6.12, 6.89-6.98, 7.07-7.15, 7.17-7.23, 7.36-7.44, 8.24.

Example 11(17)

2-{[(2E)-4-{3-[6-amino-8-oxo-7-(4-phenoxyphenyl)-7,8-dihydro-9H-purin-9-yl]-1-azetidinyl}-4-oxo-2-buten-1-yl](methyl)amino}acetamide TLC: Rf 0.30 (ethyl acetate:methanol:triethylamine=9:1:0.5);
$^1$H-NMR (CDCl$_3$): δ 2.35, 3.04, 3.23-3.25, 4.45-4.60, 4.81-4.87, 5.04-5.09, 5.37-5.47, 5.61, 6.05-6.11, 6.84-6.94, 6.99, 7.07-7.15, 7.17-7.23, 7.35-7.44, 8.24.

Example 11(18)

6-amino-9-{(3R)-1-[(2E)-4-(diethylamino)-2-butenoyl]-3-pyrrolidinyl}-7-(4-phenoxyphenyl)-7,9-dihydro-8H-purin-8-one TLC: Rf 0.52 (chloroform:methanol=9:1);
$^1$H-NMR (CDCl$_3$): δ 0.96-1.11, 2.21-2.43, 2.45-2.63, 2.83-3.05, 3.29, 3.52-3.78, 3.90-4.20, 4.22-4.33, 4.49, 5.10-5.28, 6.33, 6.90-7.04, 7.05-7.23, 7.34-7.47, 8.21.

Example 11(19)

6-amino-9-[(3R)-1-{(2E)-4-[(2-hydroxyethyl)(methyl)amino]-2-butenoyl}-3-pyrrolidinyl]-7-(4-phenoxyphenyl)-7,9-dihydro-8H-purin-8-one TLC: Rf 0.18 (ethyl acetate:methanol:triethylamine=9:1:0.5);
$^1$H-NMR (CDCl$_3$): δ 2.21-2.62, 2.85-3.08, 3.21-3.28, 3.52-3.74, 3.92-4.17, 4.25-4.33, 4.61-4.63, 5.13-5.30, 6.24-6.37, 6.87-6.98, 7.07-7.23, 7.35-7.44, 8.19-8.22.

Example 11(20)

6-amino-9-{1-[(2E)-4-(4-hydroxy-1-piperidinyl)-2-butenoyl]-3-azetidinyl}-7-(4-phenoxyphenyl)-7,9-dihydro-8H-purin-8-one TLC: Rf 0.30 (dichloromethane:methanol:triethylamine=9:1:0.1);
$^1$H-NMR (CDCl$_3$): δ 1.30-1.75, 1.82-1.97, 2.10-2.24, 2.65-2.82, 3.05-3.20, 3.61-3.78, 4.40-4.60, 4.78-4.86, 5.00-5.11, 5.33-5.46, 6.02-6.12, 6.84-6.98, 7.05-7.24, 7.35-7.43, 8.23.

Example 11(21)

6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one

[C 28]

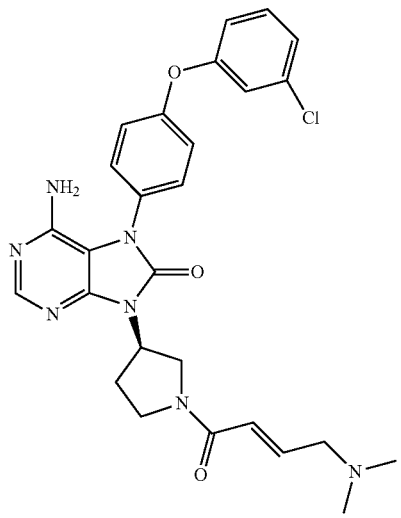

TLC: Rf 0.28 (chloroform:methanol=9:1);
$^1$H-NMR (CDCl$_3$): δ 2.17-2.43, 2.25, 2.83-3.05, 3.08, 3.51-3.76, 3.91-4.20, 4.22-4.33, 4.50, 5.10-5.18, 6.29, 6.88-7.01, 7.09, 7.10-7.20, 7.33, 7.42, 8.23.

Example 11(22)

6-amino-9-[(3S)-1-{(2E)-4-[ethyl(methyl)amino]-2-butenoyl}-3-pyrrolidinyl]-7-(4-phenoxyphenyl)-7,9-dihydro-8H-purin-8-one TLC: Rf 0.44 (ethyl acetate:methanol:triethylamine=18:2:1);
$^1$H-NMR (CDCl$_3$): δ 1.00-1.14, 2.18-2.32, 2.32-2.53, 2.82-3.06, 3.10-3.23, 3.50-3.77, 3.86-4.09, 4.09-4.35, 4.37-4.58, 5.06-5.32, 6.20-6.41, 6.87-7.03, 7.03-7.25, 7.31-7.50, 8.14-8.30.

Example 11(23)

6-amino-9-{(3S)-1-[(2E)-4-(diethylamino)-2-butenoyl]-3-pyrrolidinyl}-7-(4-phenoxyphenyl)-7,9-dihydro-8H-purin-8-one TLC: Rf 0.44 (ethyl acetate:methanol:triethylamine 18:2:1);
$^1$H-NMR (CDCl$_3$): δ 0.97-1.11, 2.19-2.46, 2.47-2.65, 2.85-3.05, 3.21-3.35, 3.50-3.76, 3.89-4.09, 4.09-4.33, 4.40-4.55, 5.10-5.28, 6.21-6.43, 6.88-7.05, 7.05-7.24, 7.34-7.48, 8.17-8.27.

Example 11(24)

6-amino-9-{1-[(2E)-4-(dimethylamino)-2-butenoyl]-3-pyrrolidinyl}-7-(4-phenoxyphenyl)-7,9-dihydro-8H-purin-8-one

[C 29]

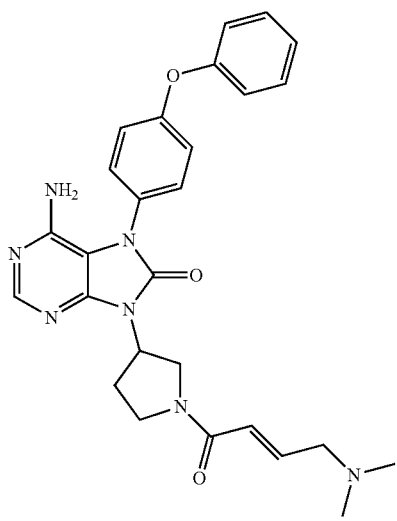

TLC: Rf 0.38 (dichloromethane:methanol:aqueous ammonia=9:1:0.1);
$^1$H-NMR (CDCl$_3$): δ 2.20-2.42, 2.83-3.14, 3.52-3.74, 3.92-4.20, 4.24-4.32, 4.42-4.51, 5.13-5.25, 6.20-6.38, 6.87-7.00, 7.05-7.24, 7.35-7.43, 8.20-8.23.

Example 11(25)

6-amino-9-({(3R)-1-[(2E)-4-(dimethylamino)-2-butenoyl]-3-pyrrolidinyl}methyl)-7-(4-phenoxyphenyl)-7,9-dihydro-8H-purin-8-one TLC: Rf 0.28 (chloroform:methanol=9:1);
$^1$H-NMR (CDCl$_3$): δ 1.75-1.97, 2.00-2.16, 2.20-2.26, 2.83-3.00, 3.02-3.10, 3.38-3.62, 3.69-3.82, 3.98-4.08, 4.50-4.60, 6.19-6.31, 6.82-6.96, 7.04-7.22, 7.35-7.43, 8.23.

Example 11(26)

6-amino-9-({(2S)-1-[(2E)-4-(dimethylamino)-2-butenoyl]-2-pyrrolidinyl}methyl)-7-(4-phenoxyphenyl)-7,9-dihydro-8H-purin-8-one TLC: Rf 0.30 (ethyl acetate:methanol:triethylamine=9:1:0.5);
$^1$H-NMR (CDCl$_3$): δ 1.86-2.27, 2.98-3.02, 3.03-3.17, 3.45-3.76, 3.88-3.95, 3.98-4.08, 4.15-4.23, 4.39-4.42, 4.47-4.57, 4.80-4.91, 6.09-6.19, 6.66-6.83, 6.94-7.03, 7.04-7.23, 7.35-7.46, 8.20-8.27.

Example 12 dimethylaminoacetaldehyde disulfite Water (1 mL) and concentrated hydrochloric acid (2.4 mL) were added to dimethylaminoacetaldehyde diethyl acetal (2.00 g) and heating was carried out for 3 hours at 40° C. Sodium disulfite (3.0 M aqueous solution, 3.6 mL) and ethanol (10 mL) were added on an ice bath and stirring was performed for 1 hour and 30 minutes at room temperature. Filtration was carried out followed by concentration. The resulting residue was evaporated to dryness under reduced pressure at 60° C. to obtain the title compound (1.29 g).

Example 13 tert-butyl (3R)-3-{[6-(dibenzylamino)-5-nitropyrimidin-4-yl]amino}pyrrolidine-1-carboxylate The title compound (27.0 g) having the physical property value given below was obtained by following the same process template as in Example 2, using the compound (19 g) produced in Example 1 and using tert-butyl (3R)-3-aminopyrrolidine-1-carboxylate (10.5 g) in place of the tert-butyl 3-aminoazetidine-1-carboxylate.

TLC: Rf 0.29 (hexane:ethyl acetate=4:1).

Example 14

6-amino-7-(4-phenoxyphenyl)-9-[(3R)-pyrrolidin-3-yl]-7,9-dihydro-8H-purin-8-one dihydrochloride The title compound (945 mg) having the physical property value indicated below was obtained by following the same process template as in Example 10, using the compound (9.0 g) produced in Example 13 and using p-phenoxyphenylboric acid (2.1 g).

TLC: Rf 0.43 (dichloromethane:methanol:aqueous ammonia=8:1:0.1).

Example 15 diethyl (2-{[(3R)-3-[6-amino-8-oxo-7-(4-phenoxyphenyl)-7,8-dihydro-9H-purin-9-yl]pyrrolidin-1-yl}-2-oxoethyl)phosphonate 1,1'-carbonyldiimidazole (0.827 g) was added to tetrahydrofuran (5 mL) and heating to 40° C. was carried out. To this solution was added diethylphosphonoacetic acid (1.00 g) dissolved in tetrahydrofuran (5 mL). Stirring was performed for 30 minutes at 40° C. The thusly produced solution (0.28 mL), the compound (50 mg) produced in Example 14, and triethylamine (0.03 mL) were added to tetrahydrofuran (0.5 mL) and stirring was performed for 1 day at room temperature. Water was added and extraction with ethyl acetate was carried out. The obtained organic layer was washed with a saturated aqueous sodium chloride solution, dried over sodium sulfate, then filtered, and concentrated. The resulting residue was evaporated to dryness under reduced pressure to obtain the title compound (53 mg) having the physical property value indicated below.

TLC: Rf 0.46 (chloroform:methanol:28% aqueous ammonia=80:10:1).

Example 16

6-amino-9-{(3R)-1-[(2Z)-4-(dimethylamino)-2-butenoyl]-3-pyrrolidinyl}-7-(4-phenoxyphenyl)-7,9-dihydro-8H-purin-8-one

[C 30]

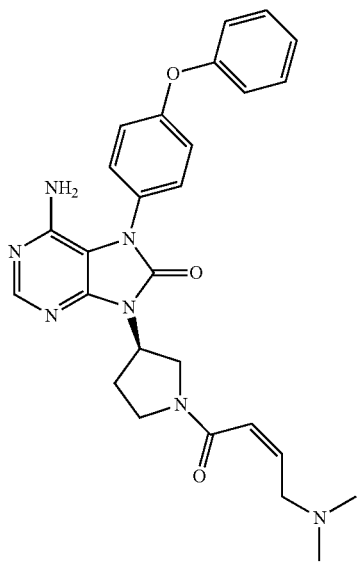

The compound (53 mg) prepared in Example 12 was added to ethanol (0.9 mL) and lithium chloride (4.2 mg) was added. Potassium hydroxide (45% aqueous solution, 0.056 mL) was added on an ice bath and the compound (25 mg) prepared in Example 15 dissolved in water (0.25 mL) was added. Stirring was carried out for 30 minutes on an ice bath. Another addition was made of the compound (7.5 mg) prepared in Example 15 dissolved in water (0.25 mL). Stirring was carried out for 2 hours on an ice bath, after which stirring was carried out for 1 day at room temperature. Extraction was performed with ethyl acetate, and the organic layer was washed with a saturated aqueous sodium chloride solution and was concentrated under reduced pressure. The resulting residue was purified by thin-layer chromatography (dichloromethane:methanol:28% aqueous ammonium=80:10:1) to obtain the title compound (7.7 mg) having the physical property values indicated below.

TLC: Rf 0.43 (chloroform:methanol:aqueous ammonia=80:10:1);

$^1$H-NMR (CDCl$_3$): δ 2.14-2.45, 2.81-3.03, 3.43-3.68, 3.80-4.06, 4.06-4.28, 4.42-4.62, 5.11-5.29, 5.97-6.24, 7.03-7.25, 8.17-8.28.

Example 17 tert-butyl 4-({[6-(dibenzylamino)-5-nitropyrimidin-4-yl]amino}methyl) piperidine-1-carboxylate The title compound (68.3 g) having the physical property value indicated below was obtained by following the same process template as in Example 2, using the compound (45.5 g) produced in Example 1 and using tert-butyl 4-(aminomethyl)piperidine-1-carboxylate (27.5 g) in place of the tert-butyl 3-aminoazetidine-1-carboxylate.

TLC: Rf 0.56 (hexan:ethyl acetate=2:1).

Example 18

6-amino-7-(4-phenoxyphenyl)-9-(piperidin-4-ylmethyl)-7,9-dihydro-8H-purin-8-one dihydrochloride The title compound (1.66 g) having the physical property value indicated below was obtained by following the same process template as in Example 10, using the compound produced in Example 17 and using p-phenoxyphenylboric acid (19 g).

TLC: Rf 0.10 (ethyl acetate:methanol:triethylamine=18:2:1).

Example 19

6-amino-9-{[1-(2-butynoyl)-4-piperidinyl]methyl}-7-(4-phenoxyphenyl)-7,9-dihydro-8H-purin-8-one

[C 31]

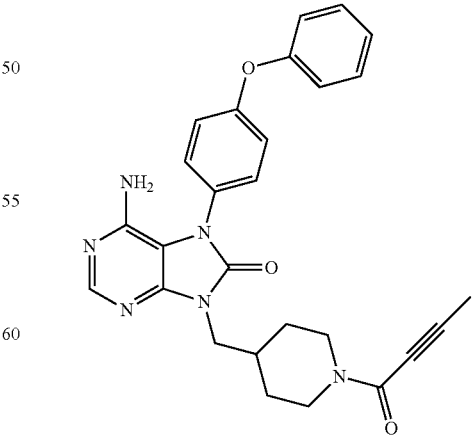

2-butynoic acid (34 mg), 1-ethyl-3-(3-dimethylaminopropyl)carbodiimide hydrochloride (EDC) (78 mg), 1-hydroxybenzotriazole (HOBt) (62 mg), and triethylamine (114 µL) were added to a dimethylformamide (3 mL) solution of the compound (100 mg) prepared in Example 18, followed by stirring for 3 hours at room temperature. Water was added to the reaction mixture and extraction with ethyl acetate was performed. The organic layer was washed with a saturated aqueous sodium bicarbonate solution and with a saturated aqueous sodium chloride solution and was then dried over anhydrous sodium sulfate and the solvent was distilled off. The residue was purified by thin-layer chromatography (dichloromethane:methanol:28% aqueous ammonia=90:10:1) to obtain the title compound (75 mg) having the physical property values indicated below.

TLC: Rf 0.43 (ethyl acetate:methanol=19:1);
$^1$H-NMR (CDCl$_3$): δ 1.21-1.45, 1.71-1.83, 1.99, 2.18-2.36, 2.59-2.72, 2.99-3.94, 4.34-4.61, 7.05-7.24, 7.36-7.43, 8.24.

Examples 19(1) to 19(49)

The exemplary compounds given below were obtained by following the same process template as in Example 9→Example 10→Example 19, using the compound prepared in Example 1, using tert-butyl (3R)-3-aminopiperidine-1-carboxylate or the corresponding amine derivative in its place, and using p-phenoxyphenylboric acid or the corresponding boric acid in its place.

Example 19(1)

6-amino-9-[1-(2-butynoyl)-3-azetidinyl]-7-(4-phenoxyphenyl)-7,9-dihydro-8H-purin-8-one TLC: Rf 0.38 (ethyl acetate:methanol=19:1);
$^1$H-NMR (CDCl$_3$): δ 1.99, 4.39-4.57, 4.75-4.83, 4.97-5.05, 5.32-5.43, 7.05-7.24, 7.35-7.43, 8.24.

Example 19(2)

6-amino-9-[(3R)-1-(2-butynoyl)-3-pyrrolidinyl]-7-(4-phenoxyphenyl)-7,9-dihydro-8H-purin-8-one

[C 32]

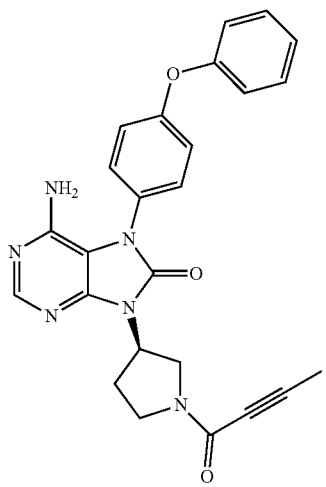 [SMILES: CC#CC(=O)N1CC[C@@H](n2c(=O)n(-c3ccc(Oc4ccccc4)cc3)c3c(N)ncnc32)C1]

TLC: Rf 0.68 (ethyl acetate:methanol=9:1);
$^1$H-NMR (CDCl$_3$): δ 1.94-2.03, 2.23-2.39, 2.80-3.01, 3.50-3.63, 3.67-3.80, 3.86-4.02, 4.03-4.18, 4.23-4.33, 4.42-4.51, 5.11-5.25, 7.04-7.23, 7.34-7.45, 8.20-8.23.

Example 19(3)

6-amino-9-[(3S)-1-(2-butynoyl)-3-pyrrolidinyl]-7-(4-phenoxyphenyl)-7,9-dihydro-8H-purin-8-one TLC: Rf 0.27 (ethyl acetate:methanol=19:1);
$^1$H-NMR (CDCl$_3$): δ 1.94-2.03, 2.24-2.40, 2.80-3.01, 3.47-3.62, 3.69-3.80, 3.89-4.00, 4.03-4.18, 4.23-4.34, 4.42-4.51, 5.13-5.25, 7.05-7.24, 7.35-7.43, 8.20-8.23.

Example 19(4)

6-amino-7-(4-phenoxyphenyl)-9-[(3R)-1-propioloyl-3-pyrrolidinyl]-7,9-dihydro-8H-purin-8-one TLC: Rf 0.51 (ethyl acetate:methanol=19:1);
$^1$H-NMR (CDCl$_3$): δ 2.25-2.43, 2.82-3.01, 3.05, 3.52-3.66, 3.73-3.85, 3.92-4.04, 4.07-4.23, 4.31-4.40, 4.48, 5.17-5.27, 7.06-7.23, 7.34-7.47, 8.23.

Example 19(5)

(2E)-4-{3-[6-amino-8-oxo-7-(4-phenoxyphenyl)-7,8-dihydro-9H-purin-9-yl]-1-azetidinyl}-4-oxo-N-phenyl-2-butenamide TLC: Rf 0.56 (ethyl acetate:methanol=19:1);
$^1$H-NMR (CDCl$_3$): δ 4.43-4.72, 4.87-4.96, 5.10-5.20, 5.40-5.52, 6.20, 6.36, 7.04-7.43, 7.72, 8.22, 12.49.

Example 19(6)

(2E)-4-{3-[6-amino-8-oxo-7-(4-phenoxyphenyl)-7,8-dihydro-9H-purin-9-yl]-1-azetidinyl}-4-oxo-2-butenamide TLC: Rf 0.50 (ethyl acetate:methanol:triethylamine=9:1:0.5);
$^1$H-NMR (DMSO): δ 4.29-4.35, 4.57-4.70, 4.86-4.91, 5.28-5.37, 5.82, 6.77-6.88, 7.10-7.20, 7.39-7.46, 7.86, 8.14.

Example 19(7)

6-amino-7-(4-phenoxyphenyl)-9-[(1-propioloyl-4-piperidinyl)methyl]-7,9-dihydro-8H-purin-8-one TLC: Rf 0.38 (chloroform:methanol=9:1);
$^1$H-NMR (CDCl$_3$): δ 1.26-1.50, 1.74-1.88, 2.19-2.38, 2.69, 3.09, 3.10, 3.91, 4.41, 4.49, 4.56, 7.05-7.23, 7.35-7.44, 8.25.

Example 19(8)

(2E)-4-{(3R)-3-[6-amino-8-oxo-7-(4-phenoxyphenyl)-7,8-dihydro-9H-purin-9-yl]-1-pyrrolidinyl}-4-oxo-2-butenamide TLC: Rf 0.41 (dichloromethane:methanol:aqueous ammonia=9:1:0.1);
$^1$H-NMR (CDCl$_3$): δ 2.23-2.47, 2.81-3.02, 3.45-3.82, 3.99-4.23, 4.35-4.53, 5.16-5.31, 5.50-5.65, 5.84-6.00, 6.97-7.30, 7.34-7.43, 8.19-8.22.

Example 19(9)

6-amino-9-[1-(2-butynoyl)-3-pyrrolidinyl]-7-(4-phenoxyphenyl)-7,9-dihydro-8H-purin-8-one

[C 33]

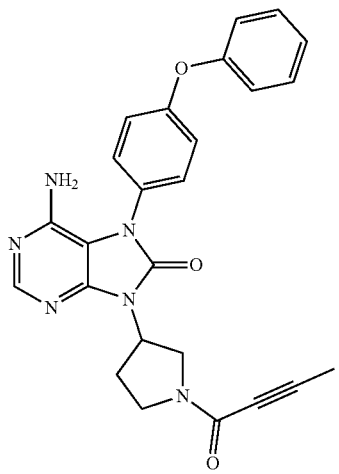

TLC: Rf 0.27 (ethyl acetate:methanol=19:1);
$^1$H-NMR (CDCl$_3$): δ 1.94-2.03, 2.24-2.40, 2.80-3.01, 3.47-3.62, 3.69-3.80, 3.89-4.00, 4.03-4.18, 4.23-4.34, 4.42-4.51, 5.13-5.25, 7.05-7.24, 7.35-7.43, 8.20-8.23.

Example 19(10)

ethyl (2E)-4-{3-[6-amino-8-oxo-7-(4-phenoxyphenyl)-7,8-dihydro-9H-purin-9-yl]-1-azetidinyl}-4-oxo-2-butenoate TLC: Rf 0.35 (ethyl acetate);
$^1$H-NMR (CDCl$_3$): δ 1.30-1.35, 4.22-4.30, 4.48-4.68, 4.84-4.90, 5.12-5.17, 5.40-5.50, 6.86-7.06, 7.07-7.16, 7.18-7.23, 7.35-7.44, 8.24.

Example 19(11)

6-amino-9-{1-[(2E)-4-phenoxy-2-butenoyl]-3-azetidinyl}-7-(4-phenoxyphenyl)-7,9-dihydro-8H-purin-8-one TLC: Rf 0.55 (ethyl acetate:methanol=19:1);
$^1$H-NMR (CDCl$_3$): δ 4.38-4.60, 4.68-4.79, 4.80-4.89, 4.99-5.11, 5.32-5.46, 6.24-6.34, 6.87-7.43, 8.22.

Example 19(12)

6-amino-9-{1-[(2E)-4-hydroxy-2-butenoyl]-3-azetidinyl}-7-(4-phenoxyphenyl)-7,9-dihydro-8H-purin-8-one TLC: Rf 0.21 (ethyl acetate:methanol=9:1);
$^1$H-NMR (CDCl$_3$): δ 1.82-1.90, 4.35-4.41, 4.43-4.62, 4.79-4.87, 5.03-5.12, 5.36-5.47, 6.19-6.26, 6.98-7.23, 7.35-7.44, 8.23.

Example 19(13)

6-amino-9-{1-[(2E)-2,4-pentadienoyl]-3-azetidinyl}-7-(4-phenoxyphenyl)-7,9-dihydro-8H-purin-8-one TLC: Rf 0.47 (ethyl acetate:methanol=9:1);
$^1$H-NMR (CDCl$_3$): δ 4.42-4.67, 4.80-4.90, 5.02-5.13, 5.33-5.50, 5.61, 6.02, 6.39-6.55, 7.04-7.27, 7.32-7.48, 8.24.

Example 19(14)

6-amino-9-[(3R)-1-(2-butynoyl)-3-pyrrolidinyl]-7-[4-(cyclohexyloxy)phenyl]-7,9-dihydro-8H-purin-8-one TLC: Rf 0.44 (ethyl acetate:methanol=19:1);
$^1$H-NMR (CDCl$_3$): δ 1.22-2.46, 1.48-1.70, 1.72-1.88, 1.94-2.05, 2.22-2.40, 2.80-3.01, 3.51-3.62, 3.68-3.80, 3.87-4.00, 4.02-4.18, 4.22-4.37, 4.42-4.55, 5.11-5.24, 6.98-7.05, 7.29-7.36, 8.19-8.23.

Example 19(15)

6-amino-9-({(3R)-1-[(2E)-4-(dimethylamino)-2-butenoyl]-3-pyrrolidinyl}methyl)-7-(4-phenoxyphenyl)-7,9-dihydro-8H-purin-8-one TLC: Rf 0.28 (chloroform:methanol=9:1);
$^1$H-NMR (CDCl$_3$): δ 1.75-1.97, 2.00-2.16, 2.20-2.26, 2.83-3.00, 3.02-3.10, 3.38-3.62, 3.69-3.82, 3.98-4.08, 4.50-4.60, 6.19-6.31, 6.82-6.96, 7.04-7.22, 7.35-7.43, 8.23.

Example 19(16)

6-amino-9-{[(2S)-1-(2-butenoyl)-2-pyrrolidinyl]methyl}-7-(4-phenoxyphenyl)-7,9-dihydro-8H-purin-8-one TLC: Rf 0.48 (ethyl acetate:methanol=9:1);
$^1$H-NMR (CDCl$_3$): δ 1.75, 3.80-2.27, 3.58-3.73, 3.94-4.04, 4.06-4.19, 4.39-4.55, 4.66-4.82, 7.03-7.22, 7.35-7.46, 8.22-8.24.

Example 19(17)

6-amino-9-[(3R)-1-(2-butynoyl)-3-pyrrolidinyl]-7-[4-(3-chlorophenoxy)phenyl]-7,9-dihydro-8H-purin-8-one TLC: Rf 0.45 (dichloromethane:methanol:aqueous ammonia=9:1:0.1);
$^1$H-NMR (CDCl$_3$): δ 1.94-2.03, 2.24-2.40, 2.80-3.01, 3.47-3.62, 3.69-3.80, 3.87-4.00, 4.03-4.19, 4.23-4.34, 4.42-4.51, 5.13-5.25, 6.93-7.00, 7.05-7.09, 7.10-7.20, 7.26-7.35, 7.38-7.44, 8.20-8.24.

Example 19(18)

6-amino-9-[(3R)-1-(2-butynoyl)-3-pyrrolidinyl]-7-[4-(3-fluorophenoxy)phenyl]-7,9-dihydro-8H-purin-8-one TLC: Rf 0.52 (ethyl acetate:methanol=19:1);
$^1$H-NMR (CDCl$_3$): δ 1.94-2.03, 2.24-2.40, 2.81-3.01, 3.51-3.62, 3.68-3.80, 3.88-4.00, 4.03-4.19, 4.23-4.34, 4.40-4.55, 5.13-5.25, 6.77-6.93, 7.12-7.20, 7.28-7.44, 8.20-8.25.

Example 19(19)

6-amino-9-[(3R)-1-(2-butynoyl)-3-pyrrolidinyl]-7-[4-(3,5-difluorophenoxy)phenyl]-7,9-dihydro-8H-purin-8-one TLC: Rf 0.48 (ethyl acetate:methanol=19:1);
$^1$H-NMR (CDCl$_3$): δ 1.94-2.03, 2.24-2.40, 2.81-3.01, 3.52-3.63, 3.68-3.80, 3.88-4.00, 4.03-4.19, 4.23-4.34, 4.42-4.54, 5.13-5.25, 6.53-6.66, 7.17-7.27, 7.41-7.48, 8.21-8.26.

Example 19(20)

6-amino-9-[(3R)-1-(2-butynoyl)-3-pyrrolidinyl]-7-(3-fluoro-4-phenoxyphenyl)-7,9-dihydro-8H-purin-8-one TLC: Rf 0.41 (ethyl acetate:methanol=19:1);
$^1$H-NMR (CDCl$_3$): δ 1.94-2.03, 2.24-2.40, 2.80-3.00, 3.52-3.63, 3.68-3.80, 3.88-4.00, 4.03-4.19, 4.23-4.34, 4.46-4.57, 5.13-5.25, 7.02-7.21, 7.29-7.42, 8.21-8.26.

Example 19(21)

6-amino-9-[(3R)-1-(2-butynoyl)-3-pyrrolidinyl]-7-[4-(4-fluorophenoxy)phenyl]-7,9-dihydro-8H-purin-8-one TLC: Rf 0.26 (ethyl acetate);
$^1$H-NMR (CDCl$_3$): δ 1.94-2.03, 2.24-2.40, 2.80-3.01, 3.47-3.62, 3.69-3.80, 3.87-4.00, 4.03-4.19, 4.23-4.34, 4.42-4.54, 5.12-5.25, 6.99-7.16, 7.35-7.41, 8.20-8.24.

Example 19(22)

6-amino-9-[(3R)-1-(2-butynoyl)-3-pyrrolidinyl]-7-[4-(4-chlorophenoxy)phenyl]-7,9-dihydro-8H-purin-8-one TLC: Rf 0.28 (ethyl acetate);
$^1$H-NMR (CDCl$_3$): δ 1.94-2.03, 2.24-2.40, 2.81-3.02, 3.47-3.62, 3.69-3.80, 3.87-4.00, 4.03-4.19, 4.23-4.34, 4.42-4.54, 5.12-5.25, 7.00-7.06, 7.09-7.17, 7.30-7.43, 8.20-8.24.

Example 19(23)

6-amino-9-[(3R)-1-(2-butynoyl)-3-pyrrolidinyl]-7-[4-(3-methylphenoxy)phenyl]-7,9-dihydro-8H-purin-8-one TLC: Rf 0.35 (ethyl acetate);
$^1$H-NMR (CDCl$_3$): δ 1.94-2.03, 2.24-2.40, 2.80-3.01, 3.47-3.62, 3.69-3.80, 3.87-4.00, 4.03-4.19, 4.23-4.34, 4.42-4.51, 5.13-5.25, 6.84-6.92, 6.99-7.03, 7.07-7.15, 7.24-7.31, 7.36-7.41, 8.20-8.24.

Example 19(24)

6-amino-9-[(3R)-1-(2-butynoyl)-3-pyrrolidinyl]-7-[4-(4-methylphenoxy)phenyl]-7,9-dihydro-8H-purin-8-one TLC: Rf 0.33 (ethyl acetate);
$^1$H-NMR (CDCl$_3$): δ 1.94-2.03, 2.22-2.42, 2.80-3.01, 3.47-3.62, 3.69-3.80, 3.87-4.00, 4.03-4.19, 4.23-4.34, 4.42-4.55, 5.13-5.25, 6.95-7.02, 7.04-7.16, 7.17-7.23, 7.33-7.41, 8.20-8.24.

Example 19(25)

6-amino-9-[(3R)-1-(2-butynoyl)-3-pyrrolidinyl]-7-{4-[3-(trifluoromethyl)phenoxy]phenyl}-7,9-dihydro-8H-purin-8-one TLC: Rf 0.33 (ethyl acetate);
$^1$H-NMR (CDCl$_3$): δ 1.94-2.03, 2.22-2.42, 2.80-3.01, 3.47-3.62, 3.69-3.80, 3.87-4.00, 4.03-4.19, 4.23-4.34, 4.42-4.55, 5.13-5.25, 7.12-7.20, 7.22-7.28, 7.35-7.38, 7.40-7.57, 8.20-8.24.

Example 19(26)

6-amino-9-[(3R)-1-(2-butynoyl)-3-pyrrolidinyl]-7-[4-(4-methoxyphenoxy)phenyl]-7,9-dihydro-8H-purin-8-one TLC: Rf 0.23 (ethyl acetate);
$^1$H-NMR (CDCl$_3$): δ 1.94-2.03, 2.24-2.40, 2.80-3.01, 3.47-3.62, 3.69-3.80, 3.83, 3.87-4.00, 4.03-4.19, 4.23-4.34, 4.41-4.55, 5.13-5.25, 6.89-6.97, 7.00-7.08, 7.30-7.38, 8.19-8.23.

Example 19(27)

6-amino-9-[(3R)-1-(2-butynoyl)-3-pyrrolidinyl]-7-[4-(3-methoxyphenoxy)phenyl]-7,9-dihydro-8H-purin-8-one TLC: Rf 0.28 (ethyl acetate);
$^1$H-NMR (CDCl$_3$): δ 1.94-2.03, 2.24-2.40, 2.81-3.01, 3.47-3.62, 3.69-3.83, 3.87-4.00, 4.03-4.19, 4.23-4.34, 4.41-4.55, 5.13-5.25, 6.62-6.69, 6.71-6.78, 7.10-7.19, 7.24-7.35, 7.36-7.42, 6.89-6.97, 7.00-7.08, 7.30-7.38, 8.20-8.24.

Example 19(28)

6-amino-9-[(3R)-1-(2-butynoyl)-3-pyrrolidinyl]-7-[4-(4-isopropylphenoxy)phenyl]-7,9-dihydro-8H-purin-8-one TLC: Rf 0.31 (ethyl acetate);
$^1$H-NMR (CDCl$_3$): δ 1.20-1.34, 1.94-2.03, 2.24-2.40, 2.81-3.01, 3.47-3.63, 3.69-3.79, 3.87-4.00, 4.03-4.19, 4.23-4.34, 4.46-4.57, 5.13-5.25, 6.98-7.03, 7.06-7.15, 7.21-7.30, 7.33-7.41, 8.20-8.24.

Example 19(29)

6-amino-9-[(3R)-1-(2-butynoyl)-3-pyrrolidinyl]-7-[4-(3-isopropylphenoxy)phenyl]-7,9-dihydro-8H-purin-8-one TLC: Rf 0.40 (ethyl acetate);
$^1$H-NMR (CDCl$_3$): δ 1.20-1.28, 1.94-2.03, 2.24-2.40, 2.81-3.01, 3.47-3.63, 3.69-3.80, 3.87-4.00, 4.03-4.19, 4.23-4.34, 4.46-4.57, 5.13-5.25, 6.84-6.90, 6.98, 7.04-7.16, 7.27-7.41, 8.20-8.24.

Example 19(30)

6-amino-9-[(3R)-1-(2-butynoyl)-3-pyrrolidinyl]-7-[4-(2-isopropylphenoxy)phenyl]-7,9-dihydro-8H-purin-8-one TLC: Rf 0.37 (ethyl acetate);
$^1$H-NMR (CDCl$_3$): δ 1.20-1.27, 1.94-2.03, 2.24-2.40, 2.81-3.01, 3.16-3.30, 3.47-3.63, 3.69-3.80, 3.87-4.00, 4.03-

4.19, 4.23-4.34, 4.46-4.56, 5.13-5.25, 6.93-7.00, 7.01-7.08, 7.17-7.24, 7.32-7.41, 8.20-8.24.

Example 19(31)

6-amino-9-[(3R)-1-(2-butynoyl)-3-pyrrolidinyl]-7-[4-(2-methylphenoxy)phenyl]-7,9-dihydro-8H-purin-8-one TLC: Rf 0.64 (ethyl acetate);
$^1$H-NMR (CDCl$_3$): δ 1.94-2.03, 2.24, 2.24-2.40, 2.81-3.01, 3.47-3.63, 3.69-3.80, 3.87-4.00, 4.03-4.19, 4.23-4.34, 4.44-4.55, 5.13-5.25, 6.98-7.05, 7.10-7.18, 7.20-7.40, 8.20-8.24.

Example 19(32)

6-amino-9-[(3R)-1-(2-butynoyl)-3-pyrrolidinyl]-7-[4-(3-chlorophenoxy)-3-methoxyphenyl]-7,9-dihydro-8H-purin-8-one TLC: Rf 0.33 (ethyl acetate);
$^1$H-NMR (CDCl$_3$): δ 1.94-2.03, 2.24-2.40, 2.82-3.01, 3.47-3.63, 3.69-3.81, 3.87-4.00, 4.03-4.19, 4.23-4.34, 4.48-4.60, 5.14-5.26, 6.85-6.92, 6.95-7.01, 7.05-7.14, 7.22-7.29, 8.23-8.27.

Example 19(33)

6-amino-9-[(3R)-1-(2-butynoyl)-3-pyrrolidinyl]-7-[4-(3,4-dichlorophenoxy)-3-methoxyphenyl]-7,9-dihydro-8H-purin-8-one TLC: Rf 0.33 (ethyl acetate);
$^1$H-NMR (CDCl$_3$): δ 1.94-2.03, 2.24-2.40, 2.82-3.01, 3.47-3.63, 3.69-3.81, 3.87, 3.87-4.00, 4.03-4.19, 4.23-4.34, 4.48-4.60, 5.14-5.27, 6.81-6.86, 6.97-7.01, 7.06-7.16, 7.37-7.40, 8.23-8.27.

Example 19(34)

6-amino-9-[(3R)-1-(2-butynoyl)-3-pyrrolidinyl]-7-(3-methoxy-4-phenoxyphenyl)-7,9-dihydro-8H-purin-8-one TLC: Rf 0.31 (ethyl acetate);
$^1$H-NMR (CDCl$_3$): δ 1.94-2.03, 2.24-2.40, 2.82-3.01, 3.47-3.63, 3.69-3.81, 3.87-4.00, 4.03-4.19, 4.23-4.34, 4.48-4.60, 5.14-5.27, 6.90-6.97, 7.00-7.04, 7.05-7.18, 7.32-7.41, 8.23-8.26.

Example 19(35)

6-amino-9-[(3R)-1-(2-butynoyl)-3-pyrrolidinyl]-7-[4-(3,4-dichlorophenoxy)phenyl]-7,9-dihydro-8H-purin-8-one TLC: Rf 0.37 (ethyl acetate);
$^1$H-NMR (CDCl$_3$): δ 1.94-2.03, 2.24-2.40, 2.81-3.01, 3.50-3.63, 3.69-3.80, 3.87-4.00, 4.03-4.19, 4.23-4.34, 4.44-4.55, 5.14-5.27, 6.92-6.98, 7.12-7.22, 7.40-7.49, 8.21-8.26.

Example 19(36)

6-amino-9-[(3R)-1-(2-butynoyl)-3-piperidinyl]-7-(4-phenoxyphenyl)-7,9-dihydro-8H-purin-8-one TLC: Rf 0.59 (ethyl acetate);
$^1$H-NMR (CDCl$_3$): δ 1.55-1.80, 1.84-2.11, 2.55-2.76, 3.07-3.21, 3.63-3.74, 4.06-4.17, 4.38-4.59, 4.60-4.74, 7.04-7.23, 7.33-7.44, 8.20-8.24.

Example 19(37)

6-amino-7-[4-(benzyloxy)phenyl]-9-[(3R)-1-(2-butynoyl)-3-pyrrolidinyl]-7,9-dihydro-8H-purin-8-one TLC: Rf 0.22 (ethyl acetate);
$^1$H-NMR (CDCl$_3$): δ 1.94-2.03, 2.24-2.40, 2.81-3.01, 3.50-3.62, 3.68-3.79, 3.87-4.00, 4.03-4.19, 4.23-4.34, 4.40-4.50, 5.08-5.27, 7.07-7.16, 7.32-7.46, 8.18-8.25.

Example 19(38)

6-amino-7-[4-(1,3-benzodioxol-5-yloxy)phenyl]-9-[1-(2-butynoyl)-3-pyrrolidinyl]-7,9-dihydro-8H-purin-8-one TLC: Rf 0.69 (ethyl acetate:methanol:aqueous ammonia=9:1:0.1);
$^1$H-NMR (CDCl$_3$): δ 1.94-2.03, 2.24-2.40, 2.80-3.01, 3.47-3.62, 3.69-3.80, 3.87-4.00, 4.03-4.19, 4.23-4.34, 4.40-4.51, 5.12-5.25, 6.01, 6.53-6.59, 6.60-6.63, 6.79-6.83, 7.04-7.13, 7.32-7.40, 8.20-8.23.

Example 19(39)

6-amino-7-(4-anilinophenyl)-9-[(3R)-1-(2-butynoyl)-3-pyrrolidinyl]-7,9-dihydro-8H-purin-8-one TLC: Rf 0.66 (ethyl acetate:methanol=9:1);
$^1$H-NMR (CDCl$_3$): δ 1.94-2.03, 2.23-2.40, 2.80-3.01, 3.50-3.62, 3.68-3.80, 3.87-4.00, 4.02-4.19, 4.23-4.34, 4.46-4.60, 5.12-5.25, 6.02, 7.00-7.18, 7.22-7.40, 8.18-8.22.

Example 19(40)

6-amino-7-(4-benzoylphenyl)-9-[(3R)-1-(2-butynoyl)-3-pyrrolidinyl]-7,9-dihydro-8H-purin-8-one TLC: Rf 0.62 (ethyl acetate:methanol=8:1);
$^1$H-NMR (CDCl$_3$): δ 1.94-2.03, 2.24-2.41, 2.81-3.01, 3.52-3.63, 3.68-3.81, 3.88-4.01, 4.03-4.20, 4.25-4.36, 4.55-4.65, 5.17-5.29, 7.49-7.68, 7.81-7.86, 7.97-8.03, 8.25-8.29.

Example 19(41)

6-amino-7-(4-benzylphenyl)-9-[(3R)-1-(2-butynoyl)-3-pyrrolidinyl]-7,9-dihydro-8H-purin-8-one TLC: Rf 0.53 (ethyl acetate:methanol=9:1);
$^1$H-NMR (CDCl$_3$): δ 1.94-2.02, 2.23-2.39, 2.80-3.00, 3.50-3.61, 3.67-3.79, 3.87-4.00, 4.02-4.18, 4.23-4.32, 4.44-4.52, 5.12-5.24, 7.18-7.42, 8.19-8.23.

Example 19(42)

6-amino-9-[(3R)-1-(2-butynoyl)-3-pyrrolidinyl]-7-[4-(phenoxymethyl)phenyl]-7,9-dihydro-8H-purin-8-one TLC: Rf 0.50 (ethyl acetate:methanol=19:1);
$^1$H-NMR (CDCl$_3$): δ 1.94-2.03, 2.25-2.40, 2.82-3.01, 3.51-3.63, 3.69-3.80, 3.88-4.01, 4.05-4.19, 4.25-4.34, 4.45-4.54, 5.11-5.27, 6.95-7.05, 7.28-7.37, 7.43-7.51, 7.60-7.66, 8.22-8.27.

Example 19(43)

6-amino-9-[(3R)-1-(2-butynoyl)-3-pyrrolidinyl]-7-{4-[(6-methyl-2-pyridinyl)oxy]phenyl}-7,9-dihydro-8H-purin-8-one TLC: Rf 0.48 (ethyl acetate:methanol=19:1);
$^1$H-NMR (CDCl$_3$): δ 1.94-2.03, 2.24-2.40, 2.46, 2.81-3.01, 3.50-3.62, 3.68-3.80, 3.87-4.01, 4.03-4.19, 4.23-4.34, 4.52-4.62, 5.14-5.27, 6.73-6.78, 6.93-6.98, 7.23-7.32, 7.40-7.46, 7.60-7.67, 8.21-8.25.

Example 19(44)

6-amino-9-[(3R)-1-(2-butynoyl)-3-pyrrolidinyl]-7-[4-(4-fluoro-3-methylphenoxy)phenyl]-7,9-dihydro-8H-purin-8-one TLC: Rf 0.51 (ethyl acetate:methanol=19:1);
$^1$H-NMR (CDCl$_3$): δ 1.94-2.03, 2.24-2.40, 2.81-3.01, 3.52-3.63, 3.68-3.80, 3.87-4.01, 4.03-4.19, 4.23-4.34, 4.42-4.54, 5.14-5.27, 6.84-6.95, 6.99-7.12, 7.34-7.41, 8.20-8.24.

Example 19(45)

6-amino-9-[(3R)-1-(2-butynoyl)-3-pyrrolidinyl]-7-[4-(4-methoxy-3-methylphenoxy)phenyl]-7,9-dihydro-8H-purin-8-one TLC: Rf 0.51 (ethyl acetate:methanol=19:1);
$^1$H-NMR (CDCl$_3$): δ 1.94-2.03, 2.23, 2.24-2.39, 2.81-3.01, 3.52-3.62, 3.68-3.80, 3.85, 3.87-4.01, 4.03-4.19, 4.23-4.34, 4.42-4.54, 5.14-5.26, 6.80-6.84, 6.85-6.93, 7.01-7.09, 7.31-7.39, 8.20-8.24.

Example 19(46)

6-amino-9-[(3R)-1-(2-butynoyl)-3-pyrrolidinyl]-7-[4-(4-fluoro-3-methoxyphenoxy)phenyl]-7,9-dihydro-8H-purin-8-one TLC: Rf 0.48 (ethyl acetate:methanol=19:1);
$^1$H-NMR (CDCl$_3$): δ 1.94-2.03, 2.24-2.40, 2.81-3.01, 3.48-3.63, 3.68-3.80, 3.87-4.01, 4.03-4.19, 4.23-4.34, 4.44-4.56, 5.14-5.26, 6.57-6.63, 6.70-6.78, 7.03-7.14, 7.37-7.43, 8.20-8.24.

Example 19(47)

6-amino-9-[(3R)-1-(2-butynoyl)-3-pyrrolidinyl]-7-[4-(3,4-dimethylphenoxy)phenyl]-7,9-dihydro-8H-purin-8-one TLC: Rf 0.53 (ethyl acetate:methanol=19:1);
$^1$H-NMR (CDCl$_3$): δ 1.94-2.03, 2.24-2.40, 2.81-3.01, 3.48-3.62, 3.68-3.80, 3.87-4.00, 4.03-4.19, 4.23-4.34, 4.48-4.59, 5.14-5.25, 6.80-6.84, 6.89, 7.04-7.17, 7.32-7.40, 8.20-8.24.

Example 19(48)

6-amino-9-[(3R)-1-(2-butynoyl)-3-pyrrolidinyl]-7-[4-(4-chloro-3-methylphenoxy)phenyl]-7,9-dihydro-8H-purin-8-one TLC: Rf 0.64 (ethyl acetate:methanol=19:1);
$^1$H-NMR (CDCl$_3$): δ 1.94-2.03, 2.24-2.40, 2.81-3.01, 3.52-3.64, 3.70-3.80, 3.87-4.00, 4.03-4.19, 4.23-4.34, 4.48-4.59, 5.14-5.25, 6.82-6.88, 6.98, 7.06-7.15, 7.33-7.42, 8.20-8.24.

Example 19(49)

6-amino-9-{(3R)-1-[(2E)-3-chloro-2-butenoyl]-3-pyrrolidinyl}-7-(4-phenoxyphenyl)-7,9-dihydro-8H-purin-8-one TLC: Rf 0.64 (ethyl acetate:methanol=19:1);
$^1$H-NMR (CDCl$_3$): δ 2.23-2.31, 2.32-2.40, 2.54-2.60, 2.86-2.97, 3.47-3.65, 2.81-3.01, 3.52-3.64, 3.84-3.88, 3.93-4.01, 4.08-4.14, 4.20-4.25, 4.40-4.54, 5.15-5.24, 6.20-6.31, 7.07-7.17, 7.18-7.22, 7.35-7.44, 8.20-8.24.

Example 20

6-amino-9-{1-[(2E)-4-(1H-benzotriazol-1-yloxy)-2-butenoyl]-3-azetidinyl}-7-(4-phenoxyphenyl)-7,9-dihydro-8H-purin-8-one

[C 34]

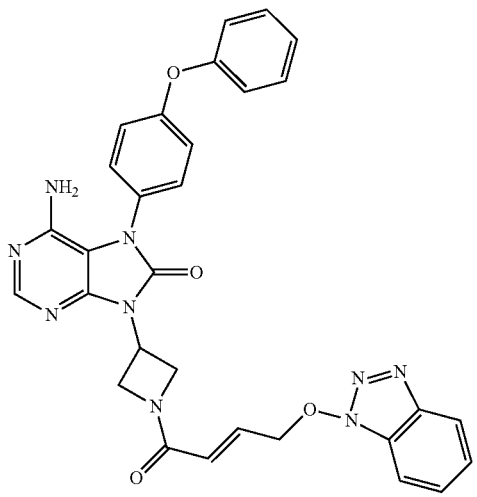

4-bromocrotonic acid (0.44 g), 1-ethyl-3-(3-dimethylaminopropyl)carbodiimide hydrochloride (0.86 g), HOBt (0.68 g), and triethylamine (1.3 mL) were added to a dimethylformamide (22 mL) solution of the compound (1.0 g) prepared in Example 7, followed by stirring for 1 hour at room temperature. Water was added to the reaction mixture and extraction with ethyl acetate was performed. The organic layer was washed with a saturated aqueous sodium chloride solution and was then dried over anhydrous sodium sulfate and the solvent was distilled off. The residue was purified by silica gel column chromatography to obtain the title compound (0.43 g) having the physical property values indicated below. TLC: Rf 0.56 (dichloromethane:methanol:28% aqueous ammonia=9:1:0.1);

$^1$H-NMR (CDCl$_3$): δ 4.43-4.63, 4.79-4.88, 4.99-5.05, 5.22-5.24, 5.35-5.45, 6.26-6.34, 7.01-7.23, 7.36-7.44, 7.51-7.62, 8.22.

Example 21

6-amino-9-[(3R)-1-(2-butynoyl)-3-pyrrolidinyl]-7-{4-[hydroxy(phenyl)methyl]phenyl}-7,9-dihydro-8H-purin-8-one A methanol (1 mL) solution of the compound (30 mg) prepared in Example 19(40) was cooled to 0° C.; sodium borohydride (2.4 mg) was added; and stirring was carried out for 30 minutes. The reaction mixture was diluted with ethyl acetate and was then washed with water and a saturated aqueous sodium chloride solution. The organic layer was dried over sodium sulfate followed by concentration under reduced pressure, and the obtained residue was purified by silica gel column chromatography (ethyl acetate→ethyl acetate:methanol=10:1) to obtain the title compound (28 mg) having the physical property values indicated below.

TLC: Rf 0.58 (ethyl acetate:methanol=9:1);

$^1$H-NMR (CDCl$_3$): δ 1.94-2.03, 2.23-2.39, 2.57, 2.80-3.00, 3.50-3.61, 3.67-3.79, 3.87-4.00, 4.02-4.18, 4.23-4.32, 4.45-4.54, 5.12-5.24, 5.91, 7.27-7.43, 7.56-7.62, 8.20-8.23.

Pharmacological Experimental Examples

Biological Example 1

Measurement (In Vitro Tests) of the Btk Inhibitory Activity and the Selectivity for Btk The Btk enzyme inhibitory activity was measured, based on the protocol provided by the manufacturer, using Btk (Invitrogen Corporation) and the Z'-LYTE™ Kinase Assay Kit-Tyr1 peptide (Invitrogen Corporation), which contained the following reagents: Tyr-1 peptide, Thy-1 phosphopeptide, 5× kinase buffer, ATP, development reagent B, development buffer, and stop reagent.

5 μL/well of a solution of the test compound diluted with dimethyl sulfoxide (DMSO), or DMSO, and 10 μL/well of the substrate/enzyme mixture solution were dispensed to a 96-well assay plate and a reaction was carried out for 20 minutes at 30° C. The substrate/enzyme mixture solution was prepared by dilution with the kinase buffer (DL-dithiothreitol (DTT, 2.7 mM), 1.33× kinase buffer) to provide a final concentration for the Tyr-1 peptide of 4 μM and a final Btk concentration of 5 nM. 5 μL/well of the adenosine triphosphate (ATP, final concentration=36 μM) was then added and a reaction was carried out for 1 hour at 30° C. After the completion of the reaction, 10 μL of a development solution, provided by diluting the development reagent B to 128× using the development buffer, was added and a reaction was carried out for an additional 1 hour at 30° C. The enzymatic reaction was then stopped by adding 10 μL of the stop solution. The fluorescence intensity at 445 nm and 520 nm in each well was measured using a Fusion Universal Microplate Analyzer (PerkinElmer Inc.) fluorescence plate reader. The percent phosphorylation was determined using the ratio of the emission at 445 nm (coumarin emission) to the emission at 520 nm (fluorescein emission) in accordance with the protocol provided with the kit.

The percent inhibition (%) by the test compound was calculated using the following equation.

[E1]

percent inhibition (%) of phosphorylation=1−{($A_C$−$A_X$)/($A_C$−$A_B$)}×100

$A_X$: % phosphorylation when the test compound has been added $A_B$: % phosphorylation in the absence of ATP addition (blank)

$A_C$: % phosphorylation when only DMSO has been added (control)

The 50% inhibition value (IC50 value) for the test compound was determined from the inhibition curve based on the % inhibition at each concentration of the test compound.

The inhibitory activity for other kinases (for example, Lck, Fyn, and LynA (all from Invitrogen Corporation) was measured in the same manner as described above using the particular kinase in place of the Btk.

According to the results, the IC50 values for the compounds of the present invention were, for example, 0.004 μM for the compound of Example 8, 0.014 μM for the compound of Example 11(3), 0.004 μM for the compound of Example 8(14), 0.007 μM for the compound of Example 19(2), and 0.011 μM for the compound of Example 19(40).

In addition, the Btk-selective inhibitory activity of the compounds of the present invention for other kinases, and particularly for Lck, Fyn, and LynA, was calculated as the ratio of the IC50 values of the individual kinases and is given in Table 1 below.

TABLE 1

| Example number | Lck [IC50]/Btk [IC50] | Fyn [IC50]/Btk [IC50] | LynA [IC50]/Btk [IC50] |
|---|---|---|---|
| 8 | 80 | 453 | 459 |
| 8(14) | 220 | 2500 | 1767 |
| 11(3) | 19 | 236 | 143 |
| 19(2) | 114 | 762 | 471 |

These results show that the compounds of the present invention not only have a Btk inhibitory activity, but also have a Btk-selective inhibitory activity with respect to other kinases.

Biological Example 2

Measurement of B Cell Activation or T Cell Activation Using Human PBMC

A 10 mmol/L solution of the test compound in DMSO was dispensed into a 96-well plate (Nunc) and a 5× dilution series was prepared using DMSO. A 100× concentration test compound dilution solution was prepared by an additional 10× dilution with RPMI1640 medium (contained 10% HI-FBS, 1% penicillin). Human peripheral blood mononuclear cells (PBMC) were diluted with the medium to provide a density of 2×10$^6$ cells/mL. 396 μL of the cell suspension was added to a 96-well plate into which 4 μL of the 100× concentration test compound dilution solution or the solvent (10% DMSO) had already been introduced and incubation was performed for 10 minutes at 37° C. and 5% CO$_2$. 10 μL of an anti-IgM antibody (Southern Biotech)/IL-4 (R & D Systems) solution or an anti-CD3/CD28 antibody bead suspension (Invitrogen Corporation) was added to a 96-well plate and 90 μL of the cell suspension prepared as described above was also added (final concentrations: anti-IgM antibody=1 μg/mL, IL-4=3 ng/mL, and anti-CD3/CD28 antibody beads=2×10$^6$ beads/mL). 10 μL of the medium was added to the unstimulated sample wells in place of these stimulating substances, and standing at 37° C. and 5% CO$_2$ was again performed. Incubation was carried out for 16 hours in the case of the evaluation of T cell activation and for 22 hours in the case of the evaluation of B cell activation. 100 μL Cytofix Buffer (BD Biosciences) was added; holding for 15 minutes at 37° C. was performed; centrifugation for 10 minutes at 1500 rpm was carried out; and the supernatant was removed. 200 µL of Perm buffer II (BD Biosciences) at −20° C. was added; holding for 30 minutes on ice was performed; centrifugation for 10 minutes at 1500 rpm was carried out; and the supernatant was removed. 0.5 mL Stain buffer (BD Biosciences) was added and centrifugation was carried out for 10 minutes at 1500 rpm. 100 µL of a mixed antibody solution was added and incubation was performed for 30 minutes on ice in the dark. The antibody was the 10× dilution with Stain Buffer of the 1:1:1 mixture of PerCP-labeled anti-CD3 antibody (BD Biosciences), AF488-labeled anti-CD20 antibody (BD Biosciences), and PE-labeled anti-CD69 antibody (BD Biosciences). 0.4 mL Stain Buffer was added and the supernatant was removed. 0.3 mL Stain Buffer was added and the cell pellet was suspended to prepare a sample for FACS measurement. The FACS analysis used a BD FACSCalibur (BD Biosciences) and CELL-Quest Version 3.3 (BD Biosciences) data analysis software. The CD69-positive signal (average fluorescence intensity) of the CD20-positive CD3-negative cells (B cells) or CD3-positive CD20-negative cells (T cells) was measured. After subtracting the value for the unstimulated sample, the % inhibition with reference to the value for the stimulated control sample was determined. The % inhibition was graphically plotted using Prism (ver. 5.01J, GraphPad Software) and the IC50 value was determined.

According to the results, the IC50 values of compounds of the present invention for the CD69-positive signal for B cells was, for example, 0.021 µM for the compound of Example 8, 0.032 µM for the compound of Example 11(3), 0.023 µM for the compound of Example 8(14), and 0.061 µM for the compound of Example 19(2). On the other hand, the IC50 values of compounds of the present invention for the CD69-positive signal for T cells was >10 µM for all of the preceding compounds. Accordingly, the compounds of the present invention were shown to have a selective inhibitory action on B cell activation.

Biological Example 3

Evaluation of the Stability in the Rat and Human Liver Microsome (1) Preparation of the Test Compound Solution A 0.25 mmol/L solution was prepared by diluting the test compound (10 mmol/L DMSO solution, 5 µL) with an aqueous 50% acetonitrile solution (195 µL).

(2) Preparation of the 0-Minute Reaction Sample

245 µL of a 0.1 mol/L phosphate buffer (pH 7.4) containing 0.5 mg/mL rat and human liver microsomes (XenoTech) and NADPH-Co-factor (BD Biosciences) was added to a reactor that had been preheated to 37° C.; pre-incubation was performed for 5 minutes; and the previously indicated test compound solution (5 µL) was added and the reaction was started. 20 µL was collected immediately after the start and the reaction was stopped by the addition to 180 µL of acetonitrile that contained an internal standard (warfarin). 20 µL of this solution was stirred with 180 µL of an aqueous 50% acetonitrile solution on a filter plate for protein depletion followed by suction filtration, and the filtrate was used as the standard sample.

(3) Preparation of the 15-Minute Reaction Sample

The previously indicated reaction solution was incubated for 15 minutes at 37° C., and 20 µL was then added to 180 µL cold acetonitrile (contained the internal standard warfarin) to stop the reaction. 20 µL of this was stirred with 180 µL of an aqueous 50% acetonitrile solution on a filter plate for protein depletion followed by suction filtration, and the filtrate was used as the standard sample.

(4) Evaluation Method and Results

The residual ratio (%) was calculated by injecting 1 µL of the sample solution into an LC-MS/MS; dividing the peak area ratio for the reaction sample (peak area for the test compound/peak area for the internal standard) by the peak area ratio for the standard sample; and multiplying the resulting value by 100.

The following were used as test compounds: compounds of the present invention and 1-{(3R)-3-[4-amino-3-(4-phenoxyphenyl)-1H-pyrazolo[3,4-d]pyrimidin-1-yl]-1-piperidinyl}-2-propen-1-one (comparative compound A) and 1-{3-[4-amino-3-(4-phenoxyphenyl)-1H-pyrazolo[3,4-d]pyrimidin-1-yl]-1-pyrrolidinyl}-2-propyn-1-one (comparative compound B), which are exemplary compounds described in Patent Document 1 that have a pyrazolopyrimidine skeleton. The residual ratio (%) of the test compound in the rat and human liver microsome was as shown in Table 2 below.

TABLE 2

| Compound | Residual ratio (%) in the rat liver microsome | Residual ratio (%) in the human liver microsome |
|---|---|---|
| Comparative compound A | 0 | 0 |
| Comparative compound B | 50.6 | 55.9 |
| Example 8 | 100 | 87.0 |
| Example 19(2) | 86.4 | 100 |
| Example 19(9) | 100 | 97.9 |
| Example 11(24) | 88.5 | 100 |

The results show that the compounds of the present invention are much more stable in rat and human liver microsomes than the comparative compounds.

Biological Example 4

Measurement of the inhibitory activity on drug-metabolizing enzymes (inhibitory action on human CYP2C8 and human CYP2C19)

[Experimental Method]

The reaction was carried out in a 96-well plate. The positive control substances (CYP2C8: ketoconazole, CYP2C19: tranylcypromine) were adjusted (CYP2C8: 0.6 and 6 mmol/L, CYP2C19: 0.9 and 9 mmol/L) with DMSO to concentrations that were 300 times the final concentration, and solutions were prepared (CYP2C8: 8 and 80 µmol/L, CYP2C19: 12 and 120 µmol/L) by 75× dilution with purified water that contained 2.7% acetonitrile. The test compounds were adjusted to 0.3 and 3 mol/L with DMSO and were adjusted to 4 and 40 µmol/L by 75× dilution with purified water that contained 2.7% acetonitrile. A reaction mixture was then prepared (the numerical values are final concentrations) by the addition of potassium phosphate buffer (pH 7.4), magnesium chloride (5 mol/L), substrate (CYP2C8: dibenzylfluorescein 1 µmol/L, CYP2C19: 3-cyano-7-ethoxycoumarin 25 µmol/L), and E. coli-expressed liver microsome CYP2C8 (Cypex, 10 pmol/L) and CYP2C19 (Cypex, 3 pmol/L). 100 µL of this reaction mixture and 50 µL of the test compound prepared as described above and the positive control solution prepared as described above were dispensed into each well and pre-incubation was carried out at 10 minutes for 37° C. The reaction was started by the addition of 50 µL NADPH solution (final concentration=1 mmol/L) and incubation was carried out for 30 minutes at 37° C. The fluorescence intensity was measured (CYP2C8: excitation wavelength=485 nm, fluorescence wavelength=538 nm; CYP2C19: excitation wavelength=409 nm, fluorescence wavelength=460 nm) immediately after the addition of the NADPH and after incubation for 30 minutes. The % inhibition was taken to be the % decline (% inhibition) in the fluorescence intensity in comparison to a control in which DMSO was added in place of the test compound solution and the reaction was carried out and was calculated using the following formula.

inhibition (%)=100−{(fluorescence intensity after the reaction of the test compound−fluorescence intensity prior to the reaction of the test compound)/(fluorescence intensity after the control reaction−fluorescence intensity prior to the control reaction)×100}

The IC50 value was taken to be <1 µM when the % inhibition at 1 µmol/L was at least 50%; was taken to be >10 µmol/L when the % inhibition at 10 µmol/L was not more than 50%; and in between the preceding (not more than 50% at 1 µmol/L and at least 50% at 10 µmol/L) was calculated using the following formula IC50=(50−$b$)/$a$ wherein a and b are the slope and intercept of the linear regression line y=ax+b that passes through the following two points: the concentration of 1 µmol/L, % inhibition and the concentration of 10 µmol/L, % inhibition.

The IC50 values of the comparative compounds and compounds of the present invention were measured using the measurement method described above.

The results were as follows: for comparative compound A and comparative compound B, the IC50 values for CYP2C8 were 4.7 µM and 6.9 µM, respectively, and the IC50 values for CYP2C19 were 5.6 µM and 8.1 µM, respectively. On the other hand, for the compounds of the present invention, for example, the compounds of Example 8, Example 11(3), Example 8(14), and Example 19(2), all had IC50 values for CYP2C8 and CYP2C19 of >10 µM. Accordingly, the compounds of the present invention were shown to have a lower CYP inhibitory action than the comparative compounds.

Biological Example 5

Measurement of the Cytotoxicity and Ability to Reduce the Mitochondrial Membrane Potential in Cultured Human Hepatoma Cells Tissue that maintains an aerobic equilibrium, e.g., the kidneys and heart, and tissue that is exposed to high drug concentrations and carries out drug metabolism, e.g., the liver, are known to be sensitive to mitochondrial dysfunction (*Drug Discovery Today*, 12 (17-18), 777-785, 2007). The reduction or extinction of the mitochondrial membrane potential by a drug is caused by the direct inhibition of the electron transport system, decoupling of electron transport from ATP synthase, or the opening of a mitochondrial membrane permeability transition pore. As a consequence, measurement of the mitochondrial membrane potential of liver cells can provide a parameter for hepatotoxicity.

Human liver cells were seeded into a collagen-coated 96-well plate at a cell density of 30,000 cells/well and incubation was carried out overnight in an incubator at 37° C. in 5% $CO_2$-95% air. The cultured cells were stained for 1 hour with 5,5',6,6'-tetrahydro-1,1',3,3'-tetramethyl-benzamidazolocarbocyanine iodide (JC-1) followed by treatment with the test compound. The test compound was dissolved in DMSO and then diluted with the liquid culture medium Hepatocyte Culture Medium (HCM) and added to the cells. The test compound treatment concentrations were 0, 6.25, 12.5, 25, 50, 100, 200, and 400 µmol/L. After exposure to the test compound for 24 hours, measurement was performed with a SpectraMax plate reader (Molecular Devices, LLC) at an excitation wavelength of 485 nm and a fluorescence wavelength of 538 nm and an excitation wavelength of 544 nm and a fluorescence wavelength of 590 nm. The membrane potential was determined by the ratio between the 544 nm/590 nm measurement value and the 485 nm/538 nm measurement value. After this, the ATP concentration in the cells was measured using a Celltiter Glo luminescent assay kit (Promega Corporation) in order to evaluate the cell toxicity of the test compound. The cells were lysed by the assay buffer provided with the measurement kit and the concentration of the ATP released from the cells was measured using the luciferin-luciferase enzyme activity as the index. The emission was measured using a SpectraMax plate reader. The ability of the test compound to lower the mitochondrial membrane potential and the cytotoxicity of the test compound were represented by the concentration (IC50 value) that caused a 50% decline in the mitochondrial membrane potential and ATP concentration, respectively. The ability to lower the mitochondrial membrane potential of the test compounds and the cytotoxicity of the test compounds are given in Table 3 below.

TABLE 3

| Compound | Ability to lower the mitochondrial membrane potential (IC50 (µM)) | Toxicity for human liver cells (IC50 (µM)) |
| --- | --- | --- |
| Comparative compound A | 39 | 78 |
| Comparative compound B | <6.25 | <6.25 |
| Example 8 | 324 | 290 |
| Example 19(2) | 200 | 135 |
| Example 19(9) | 181 | 97 |
| Example 11(24) | 347 | 213 |

The results showed that both of the IC50 values were lower for all of the compounds of the present invention than for the comparative compounds.

FORMULATION EXAMPLES

Formulation Example 1

The components indicated below were mixed by a standard method, filtered across a dedusting filter, filled into 5 mL ampoules, and thermally sterilized with an autoclave to obtain 10,000 ampoules that contained 20 mg active component per ampoule.

| | |
| --- | --- |
| 6-amino-9-{(3R)-1-[(2E)-4-(dimethylamino)-2-butenoyl]-3-pyrrolidinyl}-7-(4-phenoxyphenyl)-7,9-dihydro-8H-purin-8-one | 200 g |
| mannitol | 20 g |
| distilled water | 50 L |

Formulation Example 2

The components indicated below were mixed by a standard method and then tableted to obtain 10,000 tablets that contained 10 mg of the active component in each tablet.

| | |
|---|---|
| 6-amino-9-[(3R)-1-(2-butynoyl)-3-pyrrolidinyl]-7-(4-phenoxyphenyl)-7,9-dihydro-8H-purin-8-one | 100 g |
| calcium carboxymethyl cellulose (disintegrant) | 20 g |
| magnesium stearate (lubricant) | 10 g |
| microcrystalline cellulose | 870 g |

INDUSTRIAL APPLICABILITY

The compounds of the present invention are compounds that, in addition to having a Btk-selective inhibitory activity, exhibit an excellent metabolic stability and can avoid hepatotoxicity or the like, and as a consequence are useful as very safe therapeutic agents for diseases in which B cells or mast cells participate.

The invention claimed is:

1. A pharmaceutical composition comprising a compound of the following formula:

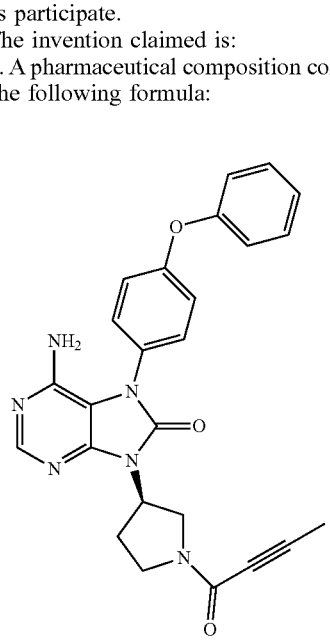

or a pharmaceutically acceptable salt thereof.

2. A pharmaceutical composition comprising a compound of the following formula:

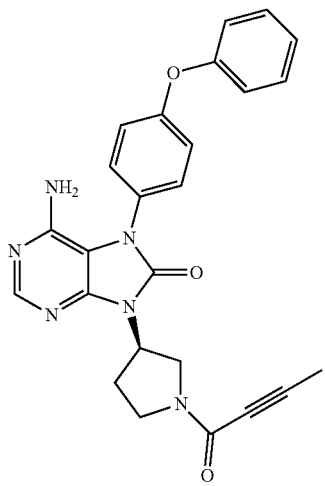 [SMILES: CC#CC(=O)N1CC[C@@H](n2c(=O)n(-c3ccc(Oc4ccccc4)cc3)c3c(N)ncnc32)C1]

or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 10,487,085 B2
APPLICATION NO. : 16/269744
DATED : November 26, 2019
INVENTOR(S) : Shingo Yamamoto et al.

Page 1 of 1

It is certified that error appears in the above-identified patent and that said Letters Patent is hereby corrected as shown below:

On the Title Page

Line 42, Column 1, Related U.S. Application Data, Line 1, Delete "(60)" and insert --(63)--

Page 2, Column 2, Other Publications, Line 51, Delete "microenvironrnent" and insert --microenvironment--

Signed and Sealed this
Eighteenth Day of February, 2020

Andrei Iancu
*Director of the United States Patent and Trademark Office*